United States Patent [19]

Mark et al.

[11] Patent Number: 5,457,043

[45] Date of Patent: Oct. 10, 1995

[54] DEGRADATION OF INDIGO AND INDIGO CARMINE WITH AN ENZYME ISOLATED FROM BACTERIA STRAIN ATCC 55396

[75] Inventors: Kai-Keung Mark; Walter Ho, both of Shatin, Hong Kong

[73] Assignee: Hong Kong Institute of Biotechnology, Shatin, Hong Kong

[21] Appl. No.: 361,105

[22] Filed: Dec. 21, 1994

Related U.S. Application Data

[62] Division of Ser. No. 12,023, Feb. 1, 1993.

[51] Int. Cl.$^6$ ............................. C12N 9/14; C12N 9/12; C12N 9/78; C12N 9/80
[52] U.S. Cl. ..................... 435/195; 435/183; 435/227; 435/228; 435/231; 435/262; 435/262.5
[58] Field of Search ........................ 435/262, 262.5, 435/183, 195, 227, 228, 231

[56] References Cited

U.S. PATENT DOCUMENTS

| | | | |
|---|---|---|---|
| 4,520,103 | 5/1985 | Ersdey, Jr. .................. | 435/121 |
| 5,173,425 | 12/1992 | Serdar et al. ................ | 435/252.3 |
| 5,374,543 | 12/1994 | Murdock ..................... | 435/122 |

*Primary Examiner*—David M. Naff
*Assistant Examiner*—L. Blaine Lankford
*Attorney, Agent, or Firm*—Meltzer, Lippe, Goldstein et al.

[57] ABSTRACT

Biologically pure strains of bacteria and enzymes therefrom capable of degrading indigo and indigo carmine are disclosed. A preferred strain is bacteria strain ATCC 55396. A method for treating water polluted with indigo or indigo carmine and decolorization of products dyed with indigo and/or indigo carmine by bringing the water into contact with the bacteria or with enzymes extracted from the bacteria is also disclosed.

2 Claims, 21 Drawing Sheets

START  OR 1.866

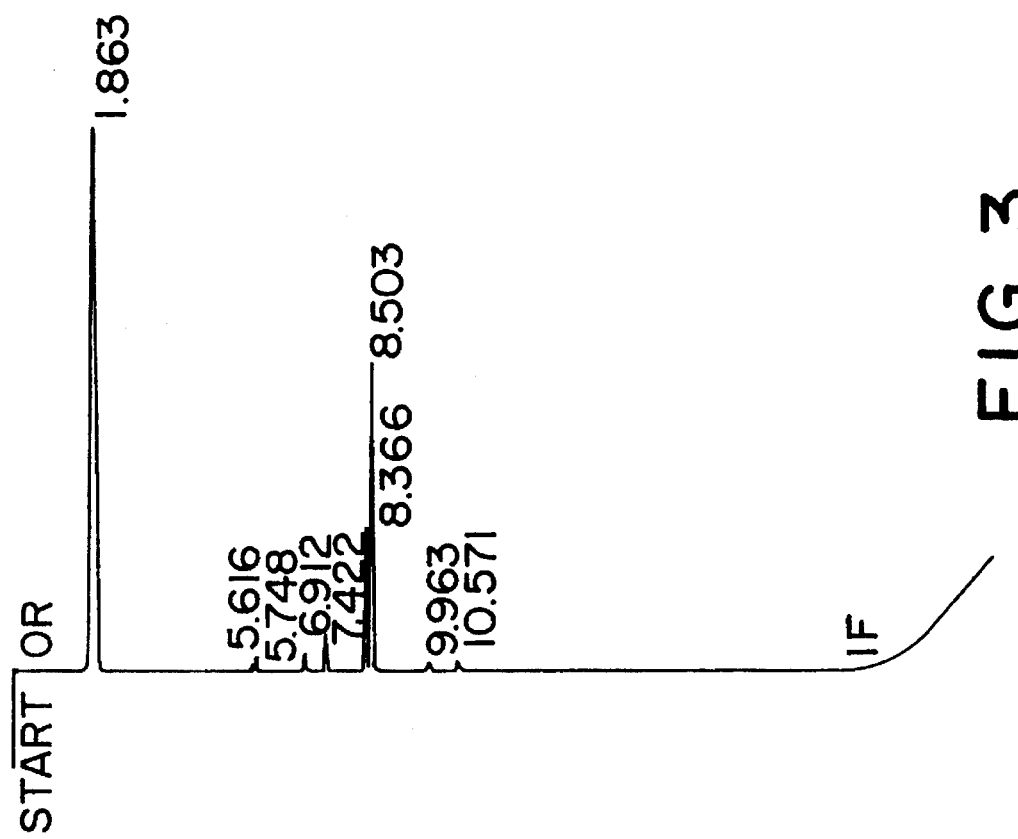

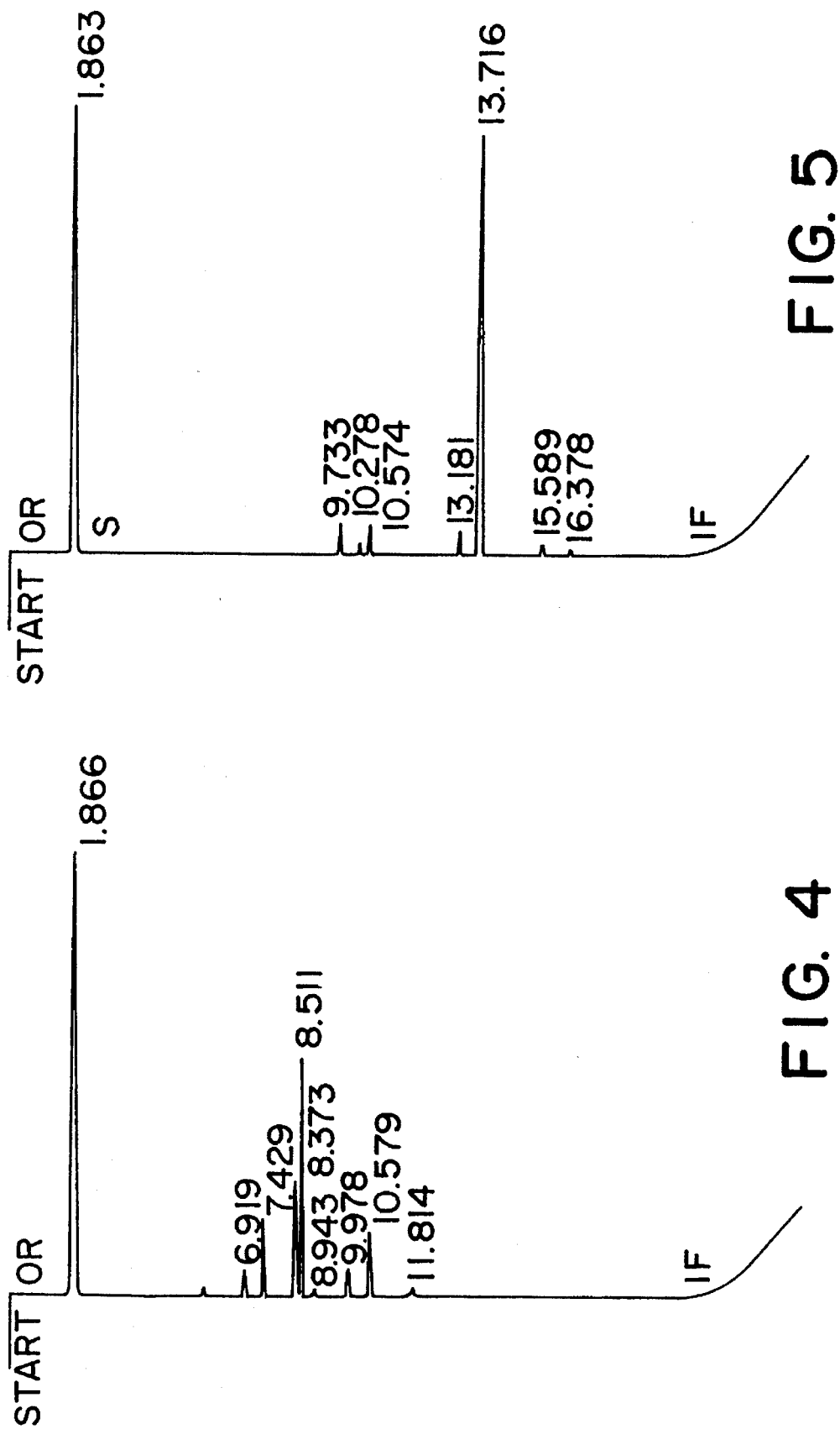

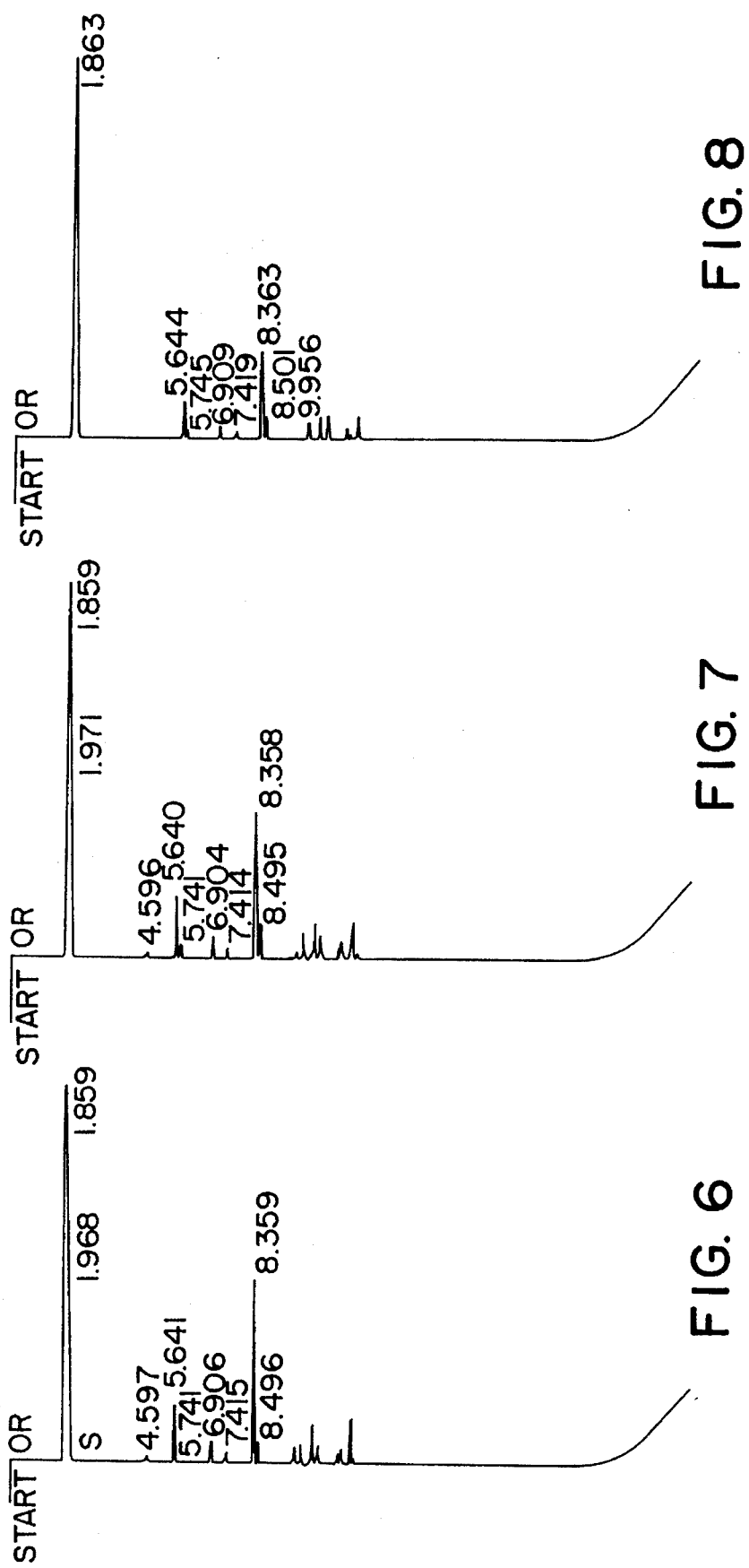

DEGRADATION OF INDIGO AND INDIGO CARMINE WITH AN ENZYME ISOLATED FROM BACTERIA STRAIN ATCC 55396

This is a division of application Ser. No. 08/012,023, filed Feb. 1, 1993.

BACKGROUND OF THE INVENTION

The present invention relates to microorganisms including bacterial strains capable of degrading indigo and indigo carmine. The present invention also relates to enzymes produced by these microbial strains which are capable of degrading indigo and indigo carmine.

Indigo is a well known dark blue dye. It is commercially available as a crystalline powder having a bronze luster. Indigo is insoluble in water, alcohol, ether, and dilute acids. It is slightly soluble in chloroform, aniline, and other non-polar organic solvents. The 5,5'-disulfonate derivative of indigo is also a blue dye known as indigo carmine. In contrast to indigo, indigo carmine is soluble in water. The chemical structures of indigo and indigo carmine are shown below.

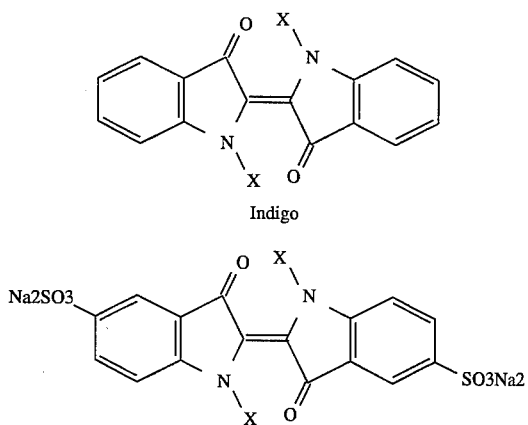

As in the case of many other dyes, the intense coloring of indigo and indigo carmine is due to the π conjugation system. Rupturing the π conjugation system of these compounds will result in decolorized products. Furthermore, because the π conjugation system of indigo and indigo carmine is the same, substances which decolorize indigo are expected to decolorize indigo carmine as well.

Indigo is used extensively as a dye by the textile industry, particularly for denim products. The annual world production of indigo exceeded 14,000 tons by 1988 (Ref: American Dye Stuff Reporter, vol. A14, p. 154 [A-06141]). In many Asian countries where denim is manufactured, such as Hong Kong, Taiwan, China, etc., indigo presents an environmental problem. For example, about 4,000 tons of indigo are imported per year into Hong Kong, of which about 350 tons per year are consumed. A significant fraction of the remaining indigo is discharged into the environment by hundreds of textile and dyeing factories. Thus, indigo is a major man-made pollutant in the water streams of many Asian countries where denim is produced.

In recent years, efforts have been made to isolate microorganisms which are capable of degrading pollutants. Among these are several microorganisms which have been isolated because of their ability to degrade dyes. Microbes capable of degrading azo dyes have been identified by Horitsu et al., 4 Eur. J. Appl. Microbial 217–224 (1977); Idaka et al., 24B. J.S.D.C. 91–94 (1978); Kulla in *Microbial Degradation of Xenobiotics and Recalcitrant Compounds*, by Leisinger, et al., 389–399, Academic Press, London (1981); and Yatome et al, 13 NA J.S.D.C. 97:166–169 (1981). The initial strains were isolated for their ability to degrade food azo dyes (see Childs et al., 16 Biochem. Pharmacol. 1551–1561 (1967) and Roxon et al., 4 Fd. Cosmot. Toxicol. 419–426 (1966)). In later years, several investigators have identified species of Pseudomonas, Bacillus, and Flavobacterium able to degrade textile azo dyes. See Wilcox et al., 21 Forest Products Journal 50–52 (1970); Horitsu et al., supra; Idaka et al., supra; Yatome et al., supra; and Kulla et al., supra. More recently, it was found that triphenyl methane and crystal violet can be degraded by the yeast Rhodotorulae and the fungus Phanerochaete. See Kwasmiewska, 34 Bull. Environ. Contam. Toxicol. 323–330 (1985), and Bumpus et al., 54 Appl. Environ. Microbial. 1143–1150 (1988).

Until now, however, there have been no reports or suggestions for isolating a microorganism, or an enzyme produced by a microorganism, capable of degrading the dyes indigo and indigo carmine.

Accordingly, it is an object of the present invention to isolate one or more microorganisms which are capable of degrading the dyes indigo and indigo carmine.

It is a further object of the invention to isolate the enzymes produced by these microorganisms which enzymes are capable of degrading the dyes indigo and indigo carmine.

It is a further object of the present invention to provide a method for treating waste water containing the dyes indigo and indigo carmine by bringing the waste water into contact with microorganisms or enzymes produced by microorganisms which are capable of degrading indigo and indigo carmine.

It is a further object of the present invention to provide a method for bleaching a substrate, such as a denim, dyed with indigo or indigo carmine by treatment of the substrate with a suspension of a microorganism or an enzyme extracted from a microorganism capable of degrading indigo and indigo carmine.

SUMMARY OF THE INVENTION

These other objects are achieved by means of the present invention according to which several microbial strains have been isolated from dye polluted waste waters which are capable of degrading indigo and indigo carmine. The microbial strain considered to be the best at degrading indigo and indigo carmine is a bacterial strain that has been given the designation H-12.

In another aspect of this invention, one or more enzymes have been extracted from isolated bacterial strains which enzymes are capable of degrading the dyes indigo and indigo carmine.

In yet another aspect of the invention, waste water polluted with indigo and indigo carmine is treated by being brought into contact with either the isolated bacterial strains or the enzymes capable of degrading the indigo and indigo carmine dyes.

In yet another aspect of the invention, a substrate, such as a denim textile, which is dyed with indigo or indigo carmine may be bleached or selectively decolorized by treatment with a suspension of a microorganism or an enzyme extracted from a microorganism capable of degrading indigo and indigo carmine. This method can be used to replace bleaching reagent in denim production, to replace stone wash treatment in denim production, and to form patterns in denim products.

BRIEF DESCRIPTION OF THE DRAWINGS

FIGS. 1–8 show fatty acid. profiles obtained on a gas chromatograph for several indigo degrading bacterial strains.

DETAILED DESCRIPTION OF THE INVENTION

A. Isolation of Indigo Degrading Microorganism

Figure 9:
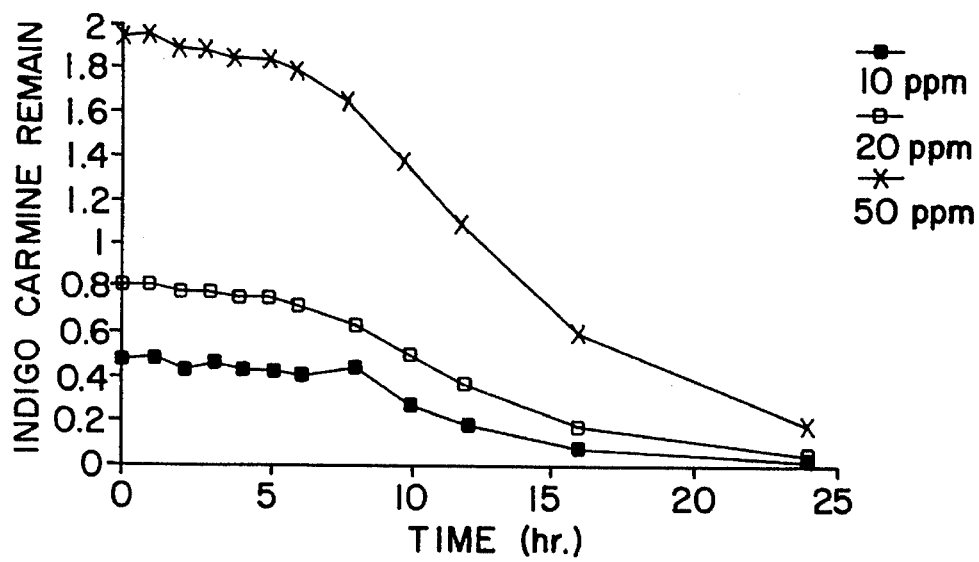
FIG. 9 illustrates the degradation of indigo carmine by the bacterial strain designated H-12.

Two methods were used to identify indigo and/or indigo carmine degrading microbes. The first of these methods, known as the halo size method, depended on the formation of a colorless halo around a colony of the microbe inoculated onto a substrate containing indigo or indigo carmine. According to this method, a rich culture medium which is commonly used in the isolation of unknown microorganisms was prepared. This culture medium, referred to as isolation medium (IM), comprised the following ingredients:

glucose 1 gram tryptone 10 grams yeast extract 1 gram $NH_4Cl$ 1 gram $H_2O$ 1 liter Assay mixtures containing indigo and indigo carmine were also prepared. Due to the insolubility of indigo in water, the indigo was ground and sieved to obtain very fine particles. After removal of the large sedimented particles, the indigo fine was made into a suspension in water, which is referred to as indigo II. Indigo II was used as the substrate in the assay mixtures for isolating indigo degrading microbes.

Petri dishes (90 mm) were filled with either 15–18 ml of IM medium supplemented with 0.1% indigo carmine, or with 18 ml IM medium substrate and a 5 ml top agar containing IM medium supplemented with 0.3–0.5% indigo II, and 1.5% agar. These preparations gave a strong blue color against a white background. Microorganisms were isolated from various locations in South China and the Petri dishes were incubated at 37° C. in the absence of light to avoid photodegradation of the indigo carmine. Degradation/decolorization of indigo and indigo carmine was observed by the formation of a transparent halo in the blue color around the colony. The size of the halo grew and was used as a measure of the degrading ability of the microorganisms. With time, the size of the colony grew as well, but for the best strains, the halo grew more rapidly than the colony. The formation of a halo suggested that the enzymes responsible for degradation were secreted as exo-enzymes.

This method worked well in identifying desirable bacterial strains when the substrate contained indigo carmine. However, the results were less successful when the substrate contained indigo. This is believed to be due to the insolubility of indigo and the problems associated therewith.

Another method used to identify indigo and indigo carmine degrading bacterial strains was a spectrophotometric method. According to this method, microbial cells were grown overnight as a stationary phase in IM liquid medium. The cells from the overnight culture were inoculated into the indigo-containing suspensions at an initial concentration of about $5\times10^8$ cell/ml. The indigo suspensions consisted of different concentrations, e.g., 0.1–3.0 mg/ml, of indigo II in IM medium or in phosphate buffer. In some cases, $Na_2CO_3$ or yeast extract was also added to the IM medium. The cells were allowed to react with the indigo in suspension at 37° C. with vigorous shaking under aerobic conditions.

The unreacted indigo and the cells were then spun down by centrifugation, and the supernatant was removed. The indigo and cells were resuspended in the original volume of $H_2O$ (usually 2 ml), and an equal volume of 98% con. $H_2SO_4$ was added to dissolve the indigo. The mixture was then incubated at 80° C. for 30 minutes to kill the cells and ensure dissolution of the indigo. The remaining indigo was then determined spectrophotometrically by measuring the absorbance at 609 nm according to the method described by Gutievrez et al., Melliand Textilberichte 71(1) E27-E28, 54-6 (1990). A standard curve correlating absorbance with the concentration of remaining indigo was obtained. From this, the degree of degradation of indigo by the microorganisms could be obtained.

A modified spectrophotometric method was also used according to which the solubilized indigo in concentrated $H_2SO_4$ was diluted one-fold with $H_2O$, after which the indigo was extracted by shaking with chloroform and dichloromethane in a 1:1 ratio. The remaining indigo was almost completely extracted into the organic phase which was then washed with $H_2O$. The absorbance of the remaining indigo in the organic solvent was measured at 609 nm and a standard curve correlating absorbance with the concentration of remaining indigo was again obtained.

When indigo carmine was used as a substrate in the assay mixture instead of indigo, the assay mixture contained the following: indigo carmine, 500 μg per 1.0 ml; phosphate buffer, pH4, 0.5 ml at 0.1M; resting cells, 1.0 ml containing $5 \times 10^8$–$10^9$ cells, and distilled $H_2O$ made up to a total of 2 ml. The assay mixture was incubated at 45° C. After a specified length of time, the assay mixture was spun down to remove the cells, and the clear supernatant containing the remaining indigo carmine was read at 609 nm and a standard curve obtained.

The following examples illustrate the results obtained by the spectrophotometric method.

EXAMPLE 1

Microbial cells were inoculated in IM medium containing 0.1 mg/ml indigo II. The starting cell concentration was about $5 \times 10^8$ cell/ml. The cultures were grown at 37° C. with vigorous aeration. The remaining indigo and cells were solubilized in concentrated $H_2SO_4$ as described above. (Organic phase extraction was not used in this case.) Spectrophotometric readings were taken at 609 nm and corrected for the absorbance of $H_2SO_4$ and cells.

By using this technique, several microbial strains were isolated which are capable of degrading indigo. These strains showed an ability to degrade 50% of the indigo present in a 24-hour period. After the initial 24-hour period, the degradation process stopped, probably due to coating of the indigo particles by an insoluble degradation product.

EXAMPLE 2

IM medium containing amounts of yeast extract ranging from 1 gm/L to 5 gm/L and 2.0 mg/ml indigo II was inoculated with microbial cells at an initial concentration of about $5 \times 10^8$ cell/ml. The cultures were incubated with vigorous shaking at 37° C. for 22 hours. The extent of indigo degradation by the microbial cells was monitored by the spectrophotometric method described above. Several biologically pure strains of bacteria and a fungal strain were isolated which are capable of degrading up to 0.6 gm/L of indigo. This compares with a typical concentration of about 0.06 gm/L indigo in textile waste water.

The microbial strains capable of degrading indigo and indigo carmine are shown in Table 1 below. It will be seen that both Gram positive and Gram negative bacterial strains as well as a fungal strain capable of degrading indigo and indigo carmine were identified. The bacterial isolates were identified based on a computerized comparison of the fatty acid profile of the isolate with the profiles of 7,000 known strains stored in a database. The apparatus used to identify the bacterial strains includes a gas chromatograph with a flame ionization detector, an autosampler, an integrator, and a computer. The identification system uses a 5% methyl phenyl silicone capillary system. After calibration of the gas chromatograph, the autosampler injects the bacterial whole cell fatty acid extracts. The integrator processes the chromatographic data and sends the data to the computer where the fatty acid peaks are identified and compared with the known fatty acid profiles stored in the database. FIGS. 1–8 show the fatty acid peaks obtained on the gas chromatograph for the bacterial strains listed in Table 1.

TABLE 1

Examples of microorganisms able to degrade indigo/indigo carmine

| Strain code | Grouping | Species name[1] | % indigo degraded[2] | Halo formation on indigo carmine plate (48 hr, 37°) |
|---|---|---|---|---|
| K-8 | Gram positive Eubacteria | *Micrococcus Luteus* Gc Subgroup A | 50% | Large halo |
| H-8 | Gram positive Eubacteria | *Bacillus cirulans* Gc Subgroup A | 81% | Large halo |
| H-12 | Gram negative Eubacteria | *Micrococcus varians* or *methylobacterium organophilum* | 78% | Large halo |
| H-15 | Gram negative Eubacteria | *Agrobacterium tumefaciens* | 77% | Large halo |
| T-24 | Gram positive Eubacteria | *Bacillus cereus/ Bacillus thuringiensis* | 69% | Large halo |
| T-26 | Gram positive Eubacteria | *Bacillus thuringiensis Bacillus cereus* | 80% | Large halo |
| 17/4-1 | Fungi | Moniliales group | not done | Medium halo |

[1]Bacterial identification system by microcheck base on fatty acid composition
[2]Indigo starting concentration 2.28 mg/ml 22 hr. incubation at 37°, pH 7 O.D. 609 nm (not ideal condition)

From these experiments, one strain of bacteria, designated H-12, was selected for further study. H-12 is considered to be the best of the indigo and indigo carmine degrading microorganisms. H-12 is believed to be a strain of either *Micrococcus varians* or *Methylobacterium organophilum*. A biologically pure culture of H-12 has been deposited in the permanent collection of American Type Culture Collection under the accession number ATCC 55396. A subculture of this microorganism may be obtained on request.

EXAMPLE 3

H-12 cells were cultured in IM medium with shaking for 16 hours at 37° C. and reached late log phase with O.D.650= 1.12, and cell density of $1.2 \times 10^9$ cells/ml. The cells were spun down and resuspended at the same cell density in citrate buffer, 0.05M, pH4, and 37° C. Indigo carmine, 500 μg/ml final concentration, O.D.609=18.0 was added to the cell culture.

The amount of indigo carmine degradation was monitored spectrophotometrically as described above. The results are illustrated in FIG. 9. The results clearly show that H-12 can completely decompose indigo carmine. Visually, H-12 was able to convert a deep blue solution (O.D.609=18) containing indigo carmine to a colorless solution within two hours. This demonstrated that H-12 can decompose indigo carmine very efficiently.

EXAMPLE 4

Samples of waste water were taken from dyeing factories. These samples contained 0.06 gm/L indigo, sodium hydroxide (NaOH), and sodium hydrosulphite ($Na_2S_2O_4$). The pH was initially 10.5–11.5 but was adjusted to pH 7 by the addition of dilute HCl.

Figure 10:
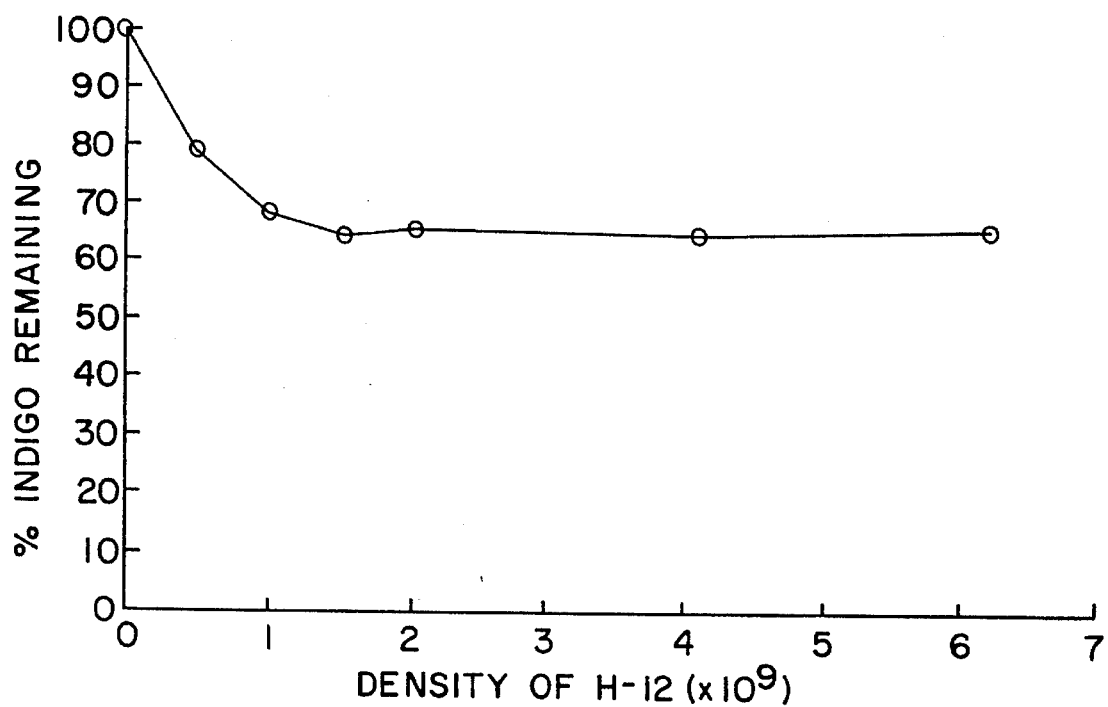
FIG. 10 illustrates the degradation of indigo polluted waste water by H-12.

H-12 cells were added to the neutralized indigo waste water at different cell concentrations ranging from $5.25 \times 10^8$ cell/ml to $6.3 \times 10^9$ cell/ml. The results after 24 hours are illustrated in FIG. 10. The results of this experiment showed that H-12 is capable of degrading about 35% of the indigo contained in industrial waste water samples.

Figure 11:
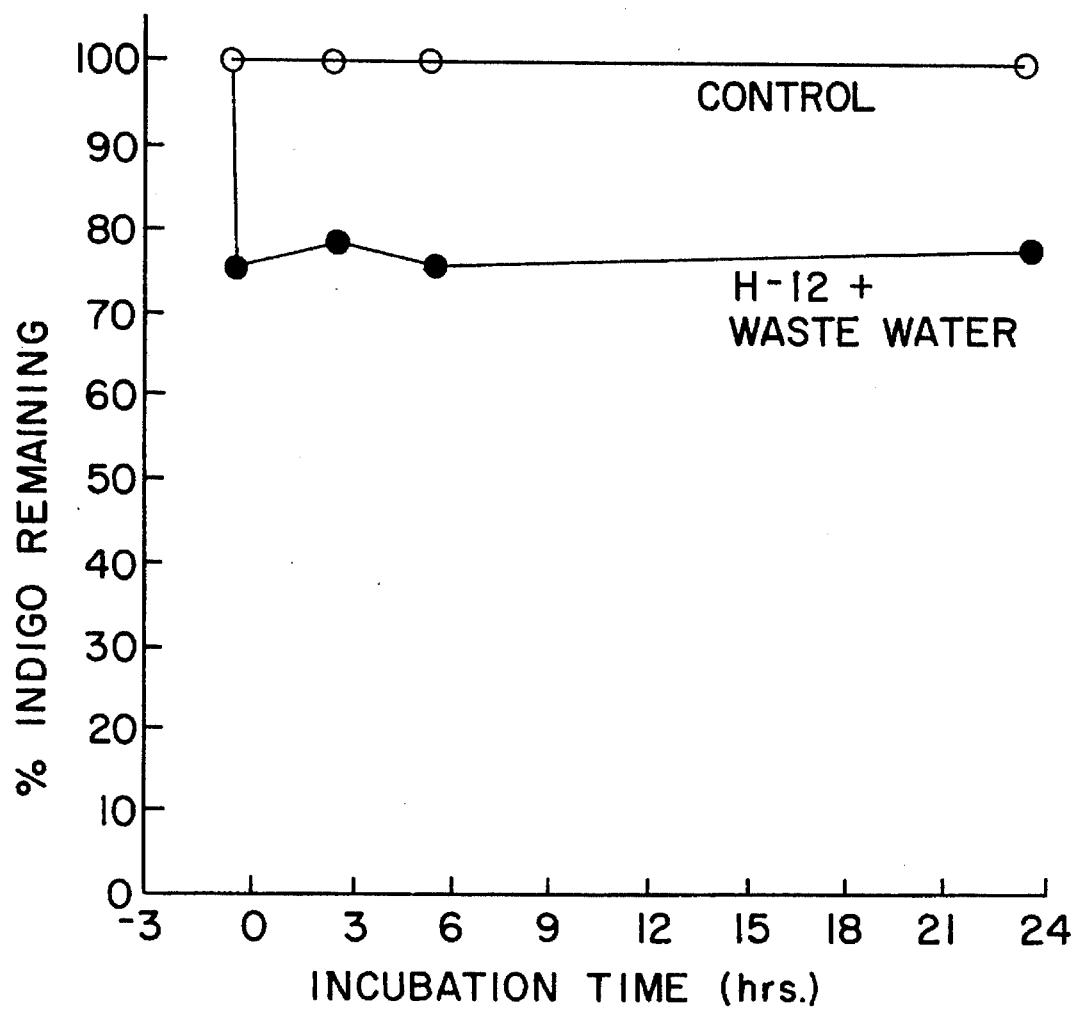
FIG. 11 also illustrates the degradation of indigo polluted waste water by H-12.

In another experiment, H-12 at a concentration of $6.2 \times 10^9$ cells/ml was added to indigo polluted waste water and the extent of indigo degradation with time was monitored during a 24 hour time period. The results are illustrated in FIG. 11. These results show that the ability of H-12 to degrade indigo was very fast initially, reaching its limit within minutes after cell-indigo contact. The degradation process stopped after about 25% of the indigo was degraded in this manner. This level of indigo degradation was not affected by an increase in cell concentration. Furthermore, finer indigo particles were degraded at a faster rate. These phenomena are consistent with a belief that the indigo particles become coated with a water-insoluble degradation product which prevents further degradation.

Further studies were carried out on H-12 and the other strains of indigo degrading bacteria. Without discussing the details of the experiments carried out, the results of these studies may be summarized as follows. When the bacteria are inoculated onto IM medium containing indigo II, they exhibit a log phase growth immediately after inoculation. However, when the strains are inoculated into media not containing indigo, the growth curves appear to go through a lag phase. This suggests that the presence of indigo induces a faster growth rate. On the other hand, it has been found that IM medium supplemented with different concentrations of indigo carmine do not appreciably stimulate or inhibit cell growth of H-12 cells. The different strains could all grow to a high cell density in IM medium. They are stable and viable for many days after reaching the stationary phase. No autolysis or rapid cell death was observed. In the case of H-12 cells grown in IM medium, even after many hours of starving these cells, the cells were found to be stable and viable, and still retained the ability to degrade indigo carmine.

H-12 was also found to grow better at 37° C. than 30° C., but did not grow at 55° C. It was also found that H-12 did not grow at pH 10, but grew well at pH 7. Starved H-12 cells gave the highest rate of indigo carmine degradation at 37° C. The rate of degradation of indigo carmine was optimal at pH 4.

The extent of indigo carmine degradation by H-12 shows an early lag period. The rate of indigo carmine degradation accelerates considerably afterwards. This suggests that the indigo carmine degrading enzyme is an inducible enzyme. To verify this idea, H-12 was grown in the presence and in the absence of indigo carmine, and then the H-12 cells were spun down and resuspended in IM medium with indigo carmine. The cell culture previously exposed to indigo carmine degraded 25.5% of the indigo carmine, while the cell culture not previously exposed to indigo carmine had only a 6.3% degradation of indigo carmine. This result confirms that the indigo carmine degrading enzyme of H-12 is inducible by its substrate indigo carmine.

B. Isolation of Indigo Degrading Enzyme

An overnight culture of H-12 was added into IM medium containing 10 g/L tryptone, 1 g/L yeast extract, 1 g/L ammonium chloride and 0.5 g/L indigo carmine. The culture was grown at 37° C. at a pH of 6.5, under static conditions with slow shaking. After 24 hours, the batch culture reached a stationary phase, and the cells were removed by centrifugation at 8000 rpm for 15 min. The supernatant was removed as a crude enzyme preparation. This enzyme preparation was frozen, lyophilized, and stored at $-20°$ C. in a freezer for later experiments.

An assay mixture was then prepared. The assay mixture comprised 1 ml of the crude enzyme preparation. A reaction mixture containing 50 µg (0.1 ml) indigo carmine, 0.5 ml citrate buffer at pH4, and 0.4 ml distilled water was also prepared and pre-incubated at 45° C. for two minutes. Then the crude enzyme preparation (1 ml) and the reaction mixture (1 ml) were mixed together producing a solution which was incubated at 45° C. for another hour. At the end of this time, the optical density of the mixture at 609 nm was measured together with that of a control. The amount of indigo carmine degraded by the enzyme could be quantified by comparing the absorbance (corrected for the control) against the standard curve for indigo carmine discussed above. It was found that indigo carmine at an initial concentration of 500 mg/L was completely degraded by the enzyme preparation from a dark blue solution to a colorless solution within 24 hours.

Further studies on the extended enzyme preparation revealed the following: as mentioned above, the indigo-degrading enzyme is apparently secreted into the medium, i.e., it is an exo-enzyme. The crude enzyme preparation (in culture supernatant) retained half of its activity even after being heated in a boiling bath for 10 minutes. This shows a high thermostability of the enzyme. The maximum degradation by the enzyme occurs at a temperature of 80° C. This again reflects the thermostability of this enzyme. The ability of the enzyme to degrade indigo carmine at different pH's was also monitored. The optimal pH was in the range of 3–3.5, although other minor maxima, e.g., at about 6.5–7.5 and at about 8.5–9.5, also occurred. The multiple maxima could mean that more than one enzyme was responsible for degradation activity. The ability of the crude enzyme preparation to degrade indigo carmine could be inactivated by protease. This implies that indigo degradation is an enzyme catalyzed reaction. The enzyme was precipitated by $(NH_4)_2SO_4$ at around 30%.

Addition of indigo carmine to the culture medium induced a higher level of enzyme production, but such enzyme was produced even in the absence of indigo carmine. Static culture had a higher level of enzyme production than shake cultures. Carbon sources such as glucose, tryptone and starch gave good cell growth and production of the enzyme, but organic salts such as citrate and acetate did poorly. The enzyme level increased dramatically in H-12 after 8 hours and peaked at 16 hours in a batch culture.

The isolated strains were also tested for their ability to degrade dyes other than indigo, such as malachite green, methyl blue, methyl green, and methyl orange. The results clearly demonstrated that the strains not only degraded indigo but also could degrade other dyes as well, at least to some degree.

The toxicity of the indigo carmine degradation product by such enzyme preparation was tested against fish (Talapia), and bacteria (*E. coli* and *B.subtilus*). No toxic effect was observed even at very high concentration (500 µg/ml).

The indigo carmine degradation products were also tested by water flea (Moina). Indigo carmine demonstrated no toxicity as expected up to 500 µg/ml, while the indigo carmine degradation products give EC50 at 40–60 µg/ml, less toxic than $K_2Cr_2O_7$ by about 5,000-fold.

The enzyme preparation can be further illustrated by reference to the following further example.

EXAMPLE 5

H-12 was grown in an overnight culture in IM medium at a pH of 7 and a temperature of 37° C. under stirring at 200 rpm. Each of six 1-liter flasks (500 ml working volume) was inoculated with 50 ml of this culture in IM medium containing 10 gm/L tryptone, 1 g/L yeast extra, 1 g/L ammonium chloride, and 0.5 g/L indigo carmine. The cultures were incubated at 200 rpm at a temperature of 37° C. The cell cultures were harvested after 19 hours during a late log growth phase. At such time, the inducer indigo carmine had been completely degraded.

A crude enzyme preparation was prepared as follows. The cells from the above cultures were removed by spinning in a centrifuge at 10,000 rpm for 20 minutes. Supernatant was passed through a 0.45 micron filter in a sterilized Millipore setup. This supernatant was then lyophilized to yield a dry powder of about 24 gm, which was stored at −20° C.

An indigo substrate was prepared as follows. Indigo powder was suspended in EDTA (0.005M) and 1-cysteine (0.03M) solution at 200 µg/ml. The settled materials were removed to give a stock solution of about 130 µg/ml fine suspension.

A plant waste water stock solution was also prepared. Plant waste water containing indigo was collected from a local textile factory and neutralized with $H_2SO_4$ to a pH of 7.2. Then, 0.186 gm of EDTA and 0.363 gm of 1-cysteine were added to 100 ml of the neutralized plant waste water containing indigo to give a final EDTA concentration of 0.005M and a 1-cysteine at a concentration of 0.03M.

Two enzyme stock solutions were also prepared. The first enzyme stock solution was prepared from 2 grams of the lyophilized crude enzyme preparation mentioned above dissolved in 6 ml of EDTA (0.005M) and 1-cysteine (0.03M) solution, at a pH 7.2, to give 0.4 mg protein/ml. The second enzyme stock solution was prepared by dissolving 1.5 gm of the lyophilized crude enzyme preparation in 5.5 ml of EDTA (0.005M) and 1-cysteine (0.03M) solution, at a pH 7.2, to give 0.33 mg protein/ml.

Next, 0.5 ml of the first enzyme stock solution was mixed with 1 ml of the indigo stock solution and the plant waste water stock solution. The mixtures were incubated at 45° C. in a water bath. After different periods of time, 1 ml of 98% conc. $H_2SO_4$ was added to the 1.5 ml samples to stop the reaction and to dissolve the remaining indigo. The mixture was well mixed and heated in a water bath at 80° C. for 30 minutes to ensure all indigo was dissolved. After cooling, 2 ml of double distilled water was added to dilute the conc. $H_2SO_4$ and 1 ml of an organic solvent (1:1 $CH_2Cl_2$:$CHCl_3$) was added to extract the dissolved indigo. This extraction was repeated six times. The pooled extract was read at 600 nm to determine the remaining indigo by comparison to a standard curve.

The results of these experiments are shown in Tables 2 and 3 below and illustrated in FIGS. 12–15.

TABLE 2

Time Response Experiment (indigo suspension preparation)

| Time (min) | O.D. 600 | % indigo degraded |
|---|---|---|
| 0 | 0.709 | — |
| 1 | 0.411 | 42.32 |
| 10 | 0.330 | 53.75 |
| 20 | 0.286 | 59.92 |
| 30 | 0.208 | 70.85 |
| 60 | 0.201 | 97.06 |

Figure 12:
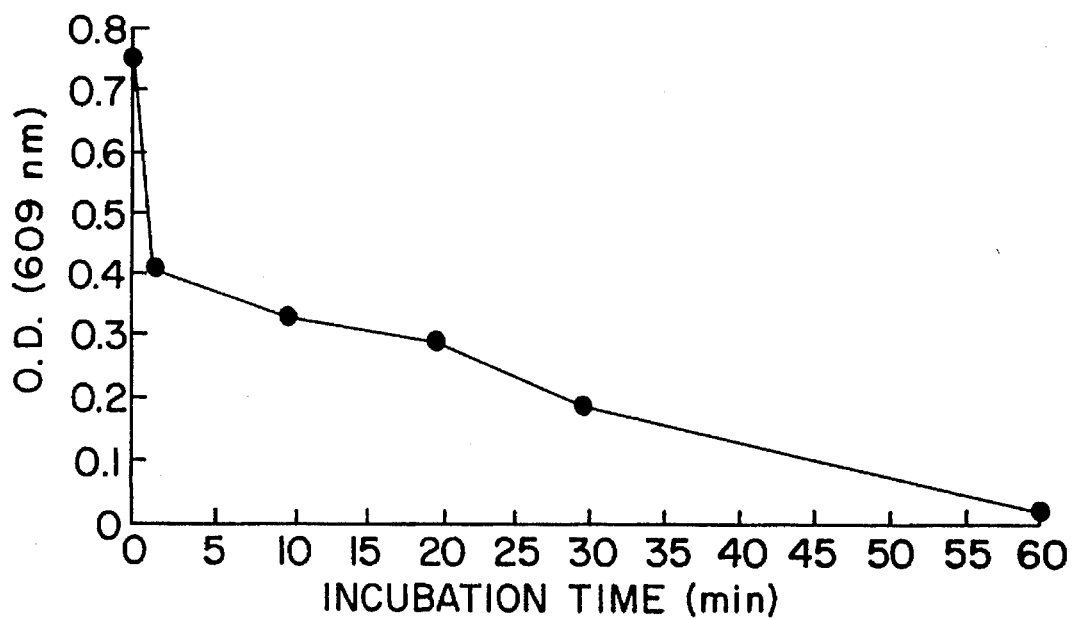
FIG. 12 illustrates the optical density of remaining indigo after an indigo containing stock solution has been treated with indigo-degrading enzyme extracted from H-12.
Figure 13:
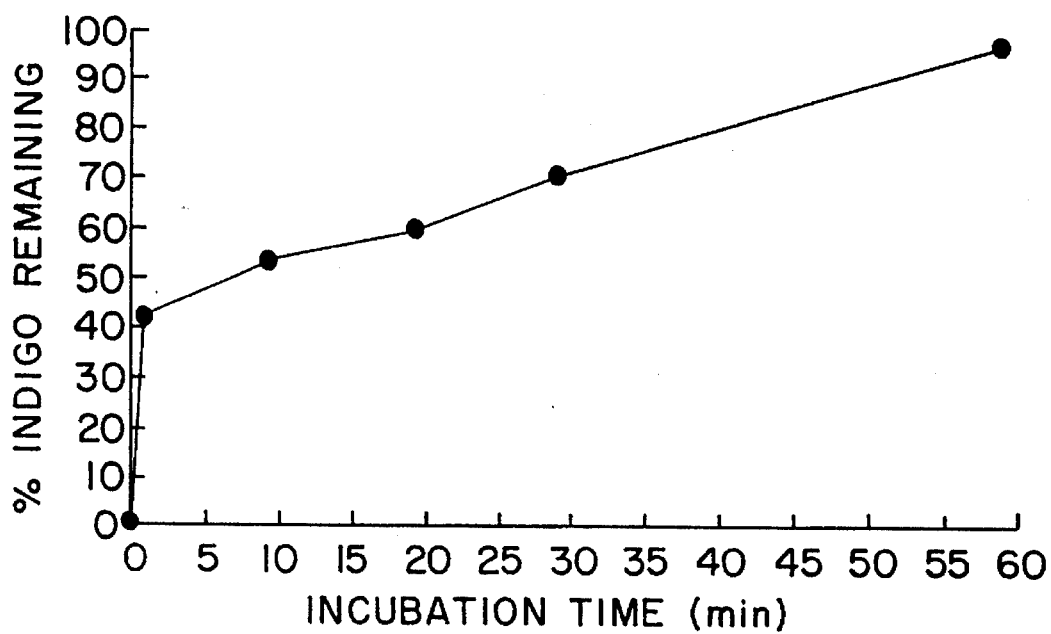
FIG. 13 illustrates the degradation of indigo in the indigo stock solution treated with the indigo-degrading enzyme extracted from H-12.

Results are also presented in FIG. 12 and FIG. 13.

TABLE 3

Time Response Experiment (Plant Waste Water)

| Time (min) | O.D. 600 | % indigo degraded |
|---|---|---|
| 0 | 0.345 | — |
| 1 | 0.114 | 68.41 |
| 10 | 0.102 | 70.44 |
| 20 | 0.090 | 74.41 |
| 30 | 0.095 | 72.46 |
| 60 | 0.045 | 85.07 |

Figure 14:
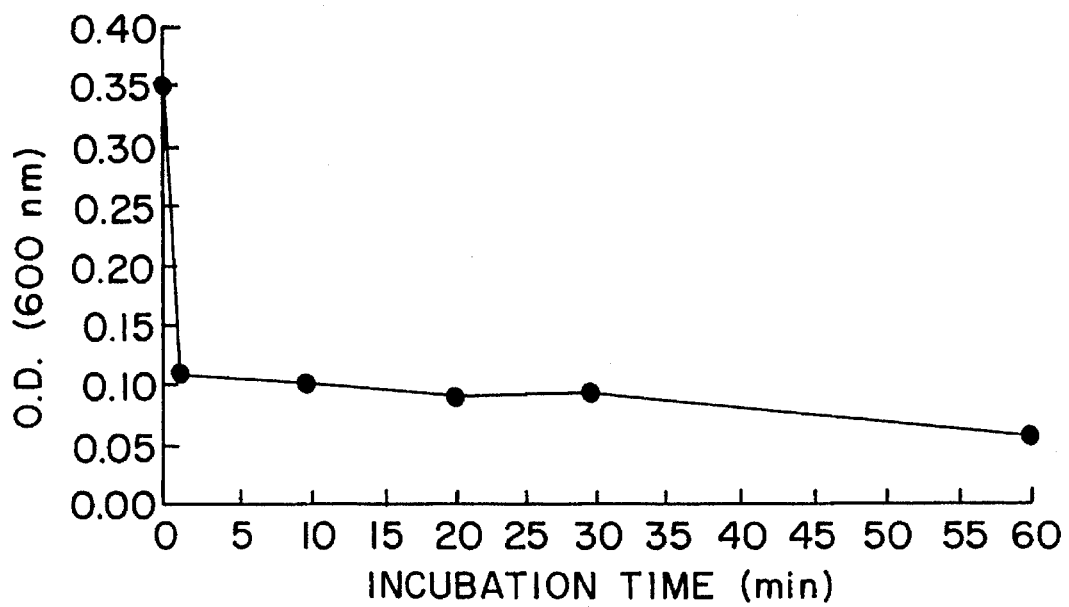
FIG. 14 illustrates the optical density of remaining indigo after an indigo polluted waste water has been treated with indigo-degrading enzymes extracted from H-12.
Figure 15:
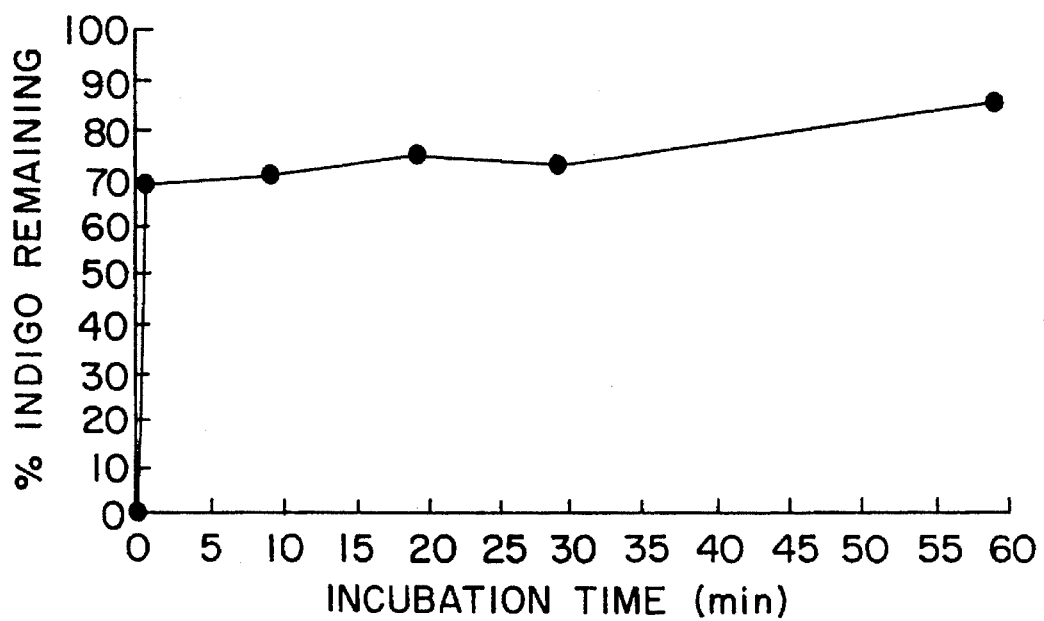
FIG. 15 illustrates the degradation of indigo in the indigo polluted waste water treated with the indigo-degrading enzymes extracted from H-12.

Results are also presented in FIG. 14 and FIG. 15

Table 2 and FIGS. 12 and 13 illustrate that virtually all of the indigo in the indigo stock solution is degraded within one hour by the enzymes extracted from H-12. Table 3 and FIG. 14 and FIG. 15 illustrate that about 85% of the indigo in the indigo polluted waste water stock solution is degraded within one hour by the H-12 enzyme extract. In addition to the above, a series of dose response experiments were performed according to which the degree to which different concentrations of the lyophilized crude enzyme could degrade the indigo in the indigo stock solution was measured. The results are shown in Table 4 below.

TABLE 4

Dose response (indigo suspension preparation)

| Enzyme conc. g/ml | Time (min) | O.D. 600 | % indigo degradation |
|---|---|---|---|
| Control | | | |
| (A) 0.286(1) | 0 | 0.510 | 0 |
| | 1 | 0.131 | 61.40 |
| | 10 | 0.127 | 61.99 |
| | 30 | 0.109 | 78.65 |
| (B) 0.143(½) | 0 | 0.510 | 0 |
| | 1 | 0.283 | 44.50 |
| | 10 | 0.214 | 58.03 |
| | 30 | 0.206 | 59.60 |
| (C) 0.071(¼) | 0 | 0.510 | 0 |
| | 1 | 0.359 | 29.59 |
| | 10 | 0.234 | 37.24 |
| | 30 | 0.233 | 41.37 |
| (D) 0.036(⅛) | 0 | 0.510 | 0 |
| | 1 | 0.389 | 11.58 |
| | 10 | 0.339 | 33.52 |
| | 30 | 0.315 | 38.23 |

The second enzyme stock solution described above was subjected to a Bio-Rad protein assay using bovine albumin standards. It was found that the lyophilized extract contained mostly unconsumed medium and only 1.20 mg protein/gm material.

Further studies on the catalytic properties of the indigo degrading enzyme were carried out as follows.

1. Cell culture

H-12, the indigo degrading strain, was grown as an overnight culture in IM medium pH 7, 37° C., 200 rpm. Each of six 1-liter flasks (500 ml working volume) was inoculated with 50 ml of this culture in IM medium containing 10 g/L Tryptone; 1 g/L Yeast Extract; 1 g/L ammonium chloride; and 0.5 g/L indigo carmine. The cultures were incubated at 200 rpm 37° C. The cell cultures were harvested after 14–19 hr. at late log phase. At such time, the inducer indigo carmine added was completely degraded, 2. Crude enzyme preparation and lyophilized enzyme preparation The cells from the above 3L culture were removed by centrifuge at 10,000 rpm for 20 minutes in a Sorvall centrifuge. The enzyme preparation at this stage was referred to as crude enzyme preparation. The supernatant was passed through 0.45 μ Millipore filter in a sterilized Millipore apparatus. This supernatant was then lyophilized in Virtis Freeze Mobile 6 to yield a dry powder of about 24 gm, which was stored at −20° C. The enzyme preparation at this stage was referred to as lyophilized enzyme preparation.

3. Enzyme activity measurements

Method I. Indigo carmine as substrate

The assay mixture contained indigo carmine, 200 μg/ml final dilution or as specified; EDTA, 0,005M final dilution; L-cysteine, 0.03M final dilution, lyophilized crude enzyme preparation, 200 μg/ml (0.24 μg/ml protein), with resulting pH at pH 5.5–6.1. The assay mixture was incubated for 30 minutes or for a specified time period at 45° C. The optical density change was measured at O.D. 609 nm by DU-7 spectrophotometer continuously. A solution of EDTA (0.005M) and L-cysteine (0.03M) was used to replace the enzyme Solution as negative control. The level of dissolved oxygen in the assay mixture and the enzyme preparation was reduced by flushing with nitrogen. After the enzyme was added to the assay mixture and properly mixed, mineral oil was added on top to prevent further diffusion of oxygen.

Method II. Indigo carmine as substrate

The assay mixture contained 1 ml crude enzyme preparation (in IM medium), indigo carmine at 50 μg/ml final dilution or as specified, pH 4, adjusted by citrate buffer 0.05M. The assay mixture 2 ml was incubated at 45° C. for 1 hr or specified time before the optical density was measured at O.D. 609 nm. 1 ml IM medium was used to substitute the enzyme for negative control.

Method III. Indigo as substrate

Enzyme stock solution was prepared by dissolving 2 gm of lyophilized crude enzyme preparation in 6 ml of EDTA (0.005M) and L-cysteine (0.03M) solution, pH 7.2 to give 0.4 mg protein/ml (see protein determination below).

0.5 ml enzyme stock solution was mixed with 1 ml indigo stock solution. The mixture was incubated at 45° C. in a water bath. Then 1 ml of 98% conc. $H_2SO_4$ was added to 1.5 ml sample which was drawn at 30 min and 60 min to stop the reaction and to dissolve the indigo. This mixture was well mixed, heated in a water bath of 80° C. for 30 min to ensure all indigo was dissolved. After cooling, 2 ml of double distilled water was added to dilute the conc. $H_2SO_4$, and 1 ml organic solvent (1:1 $CH_2Cl_2$:$CHCl_3$) was added to extract the dissolved indigo. This extraction was repeated six times. The pooled extract was read at 600 nm to determine the remaining indigo compared to a standard curve.

The control solution contained 0.5 ml of EDTA (0.005M) and L-cysteine (0.03M) without the enzyme.

4. Indigo carmine standard curve

Figure 16A:
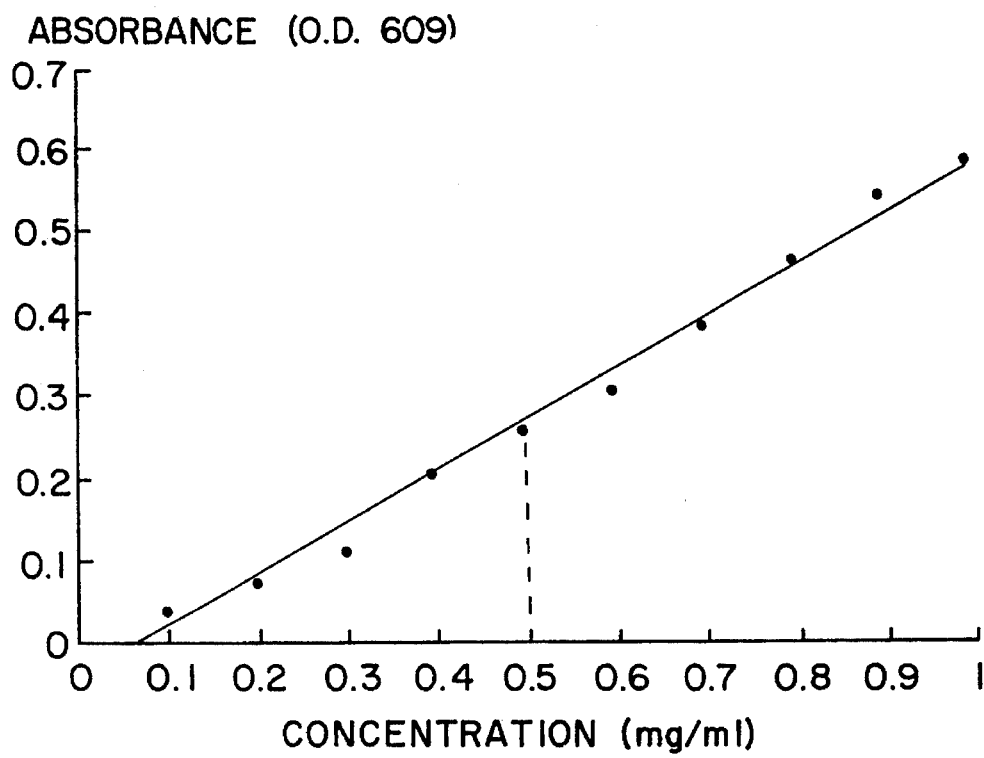
FIGS. 16a–16b show standard absorbance curves for indigo carmine at 609 nm.
Figure 16B:
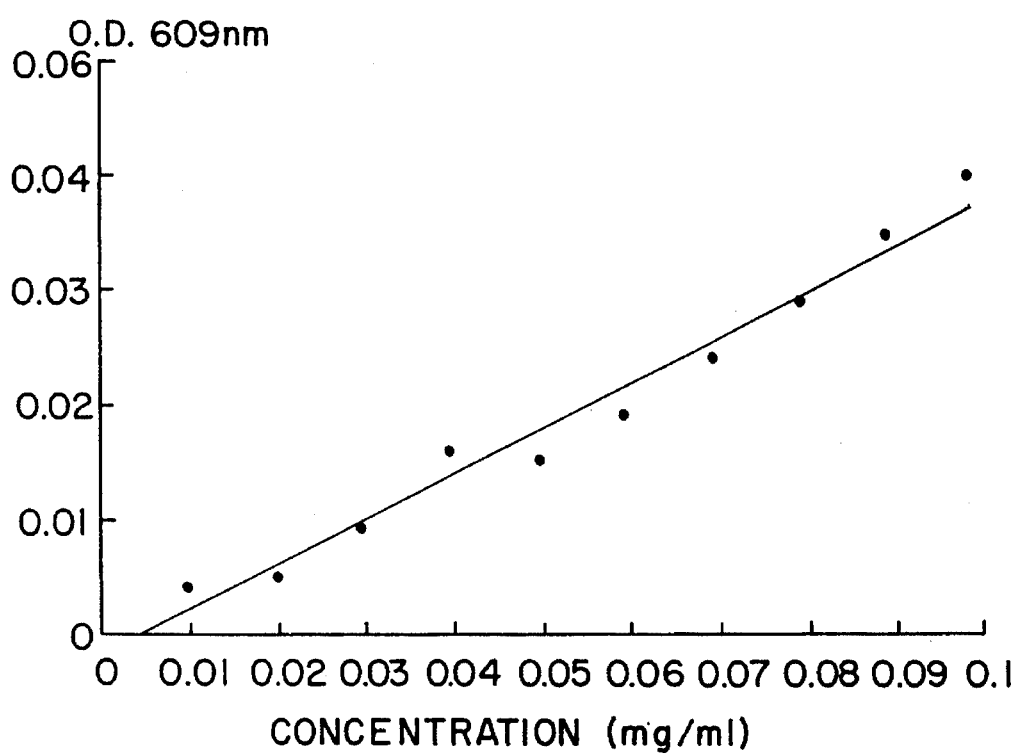

Indigo carmine has maximum absorption at 609 nm, and this feature was used to correlate optical density and concentration of indigo carmine. A standard curve was constructed (see FIGS. 16a–16b)

5. Indigo standard curve

Figure 17:
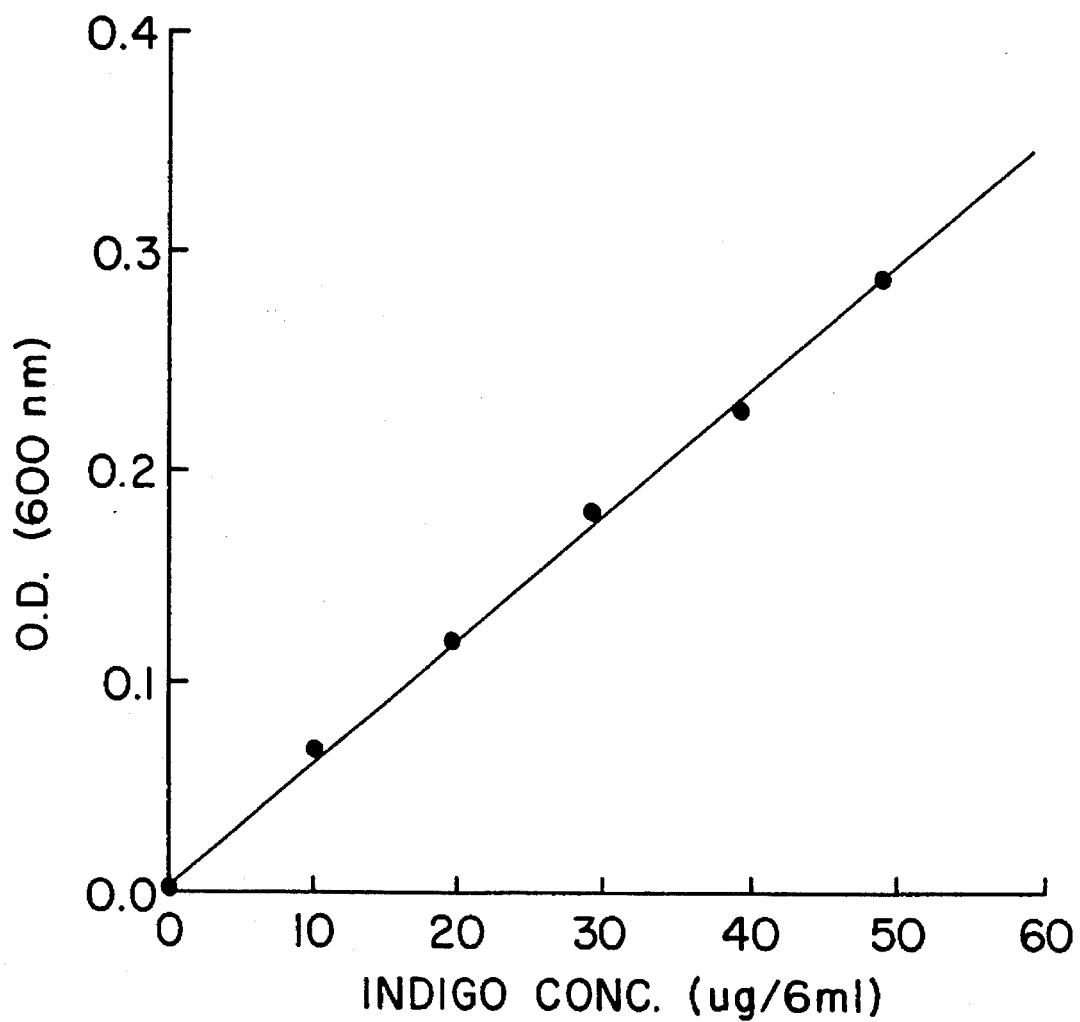
FIG. 17 shows a standard absorbance curve for indigo at 600 nm.

The standard curve (see FIG. 17) for the correlation of O.D. reading to indigo concentration was established with the same procedures outlined above in method III.

6. Indigo substrate preparation

Indigo (Sigma) powder was obtained by grinding in a mortar and suspending in a EDTA (0.005M) and L-cysteine (0.03M) solution at a proportion of 200 μg/ml. The settled materials were removed to give a stock solution of about 130 μg/ml fine suspension.

7. Protein Determination

The lyophilized crude enzyme preparation contained mostly unconsumed medium chemicals and 1.20 mg protein/gm material as determined by Bio-Rad protein assay method using bovine albumin standards.

A. Protein properties of the indigo-degrading activity

Inactivation by protease treatment

Figure 18:
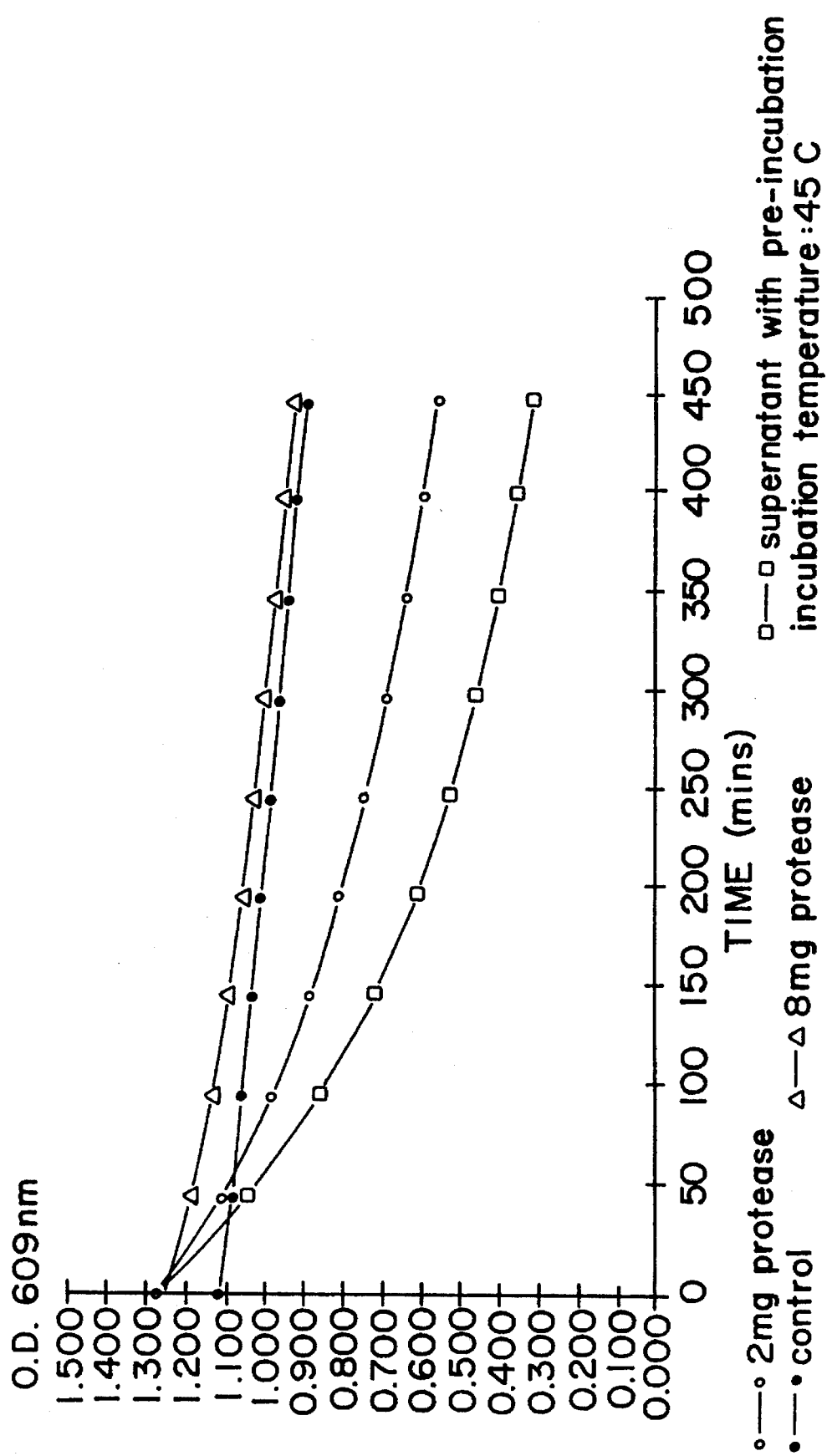
FIG. 18 shows that the indigo carmine degrading activity of an enzyme extracted from H-12 is inactivated by protease.

The crude enzyme preparation was digested by protease (Sigma) at concentrations of 8 mg/ml, 2 mg/ml, and 0 mg/ml protease at 37° C. for 3 hrs. The indigo carmine degrading activity of the digested crude enzyme preparation was assayed by method II at 45° C. and pH 3. Optical density (O.D. 609 nm) was followed by DU-7 spectrophotometer for 8 hrs. as shown in FIG. 18. The undigested crude enzyme preparation demonstrated a steady degradation of indigo carmine as reflected by the drop of O.D. 609 reading. The indigo-degrading ability was totally lost after incubating with 8 mg/ml protease, and behaved exactly as the distilled water control. The indigo carmine degrading activity was partially lost after digestion with 2 mg/ml protease. This experiment demonstrates that the indigo carmine (indigo) degrading activity is a protein.

Macromolecular nature of the degradative activity

The enzyme preparation (1300 ml) was obtained from a H-12 strain culture grown for 20 hours at 37° C. in LB medium (Tryptone, 1%; yeast extract, 0.5%; NaCl, 1%). The cells were removed and lyophilized to yield 13.0 gm of materials which was resuspended in 100 ml 0.075M, pH 7.0 phosphate buffer dialysed against 2L of the same phosphate buffer with 3 changes every 3 hr. The dialysis bag used was Spectrapor membrane tubing No. 3, 23 mm, with molecular cut-off at about 3,500D. The dialysed enzyme solution was again lyophilized to yield 4.5 gm.

The dialysed and lyophilized enzyme preparation (0.2 gm) was dissolved in 2 ml phosphate buffer, and loaded into the G50 Sephadex column (height 44 cm, ID 1.5 cm.), which was prewashed and equilibrated with phosphate buffer, 0.075M, pH 7.0 and had a flow rate of 0.15 ml/min. A total of 68 fractions (2 ml each) were collected in a 5 day period. The elution profile is presented in FIG. 19.

Figure 19:
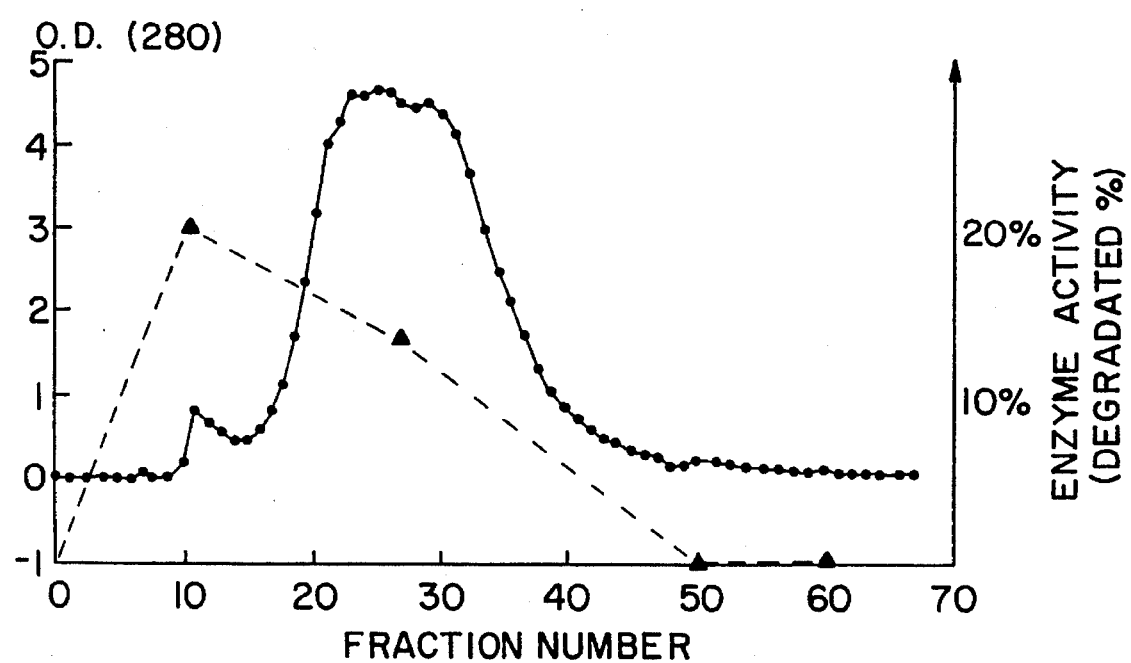
FIG. 19 shows an elution profile for an enzyme extracted from H-12.

The indigo degrading activity was found in the first peak eluted in the gel filtration experiments. (FIG. 19 and Table 5 below). SDS Polyacrylamide gel electrophoresis (7%) showed that the active fraction contained proteins of molecular weight from 40,000D to 60,000D.

Figure 20:
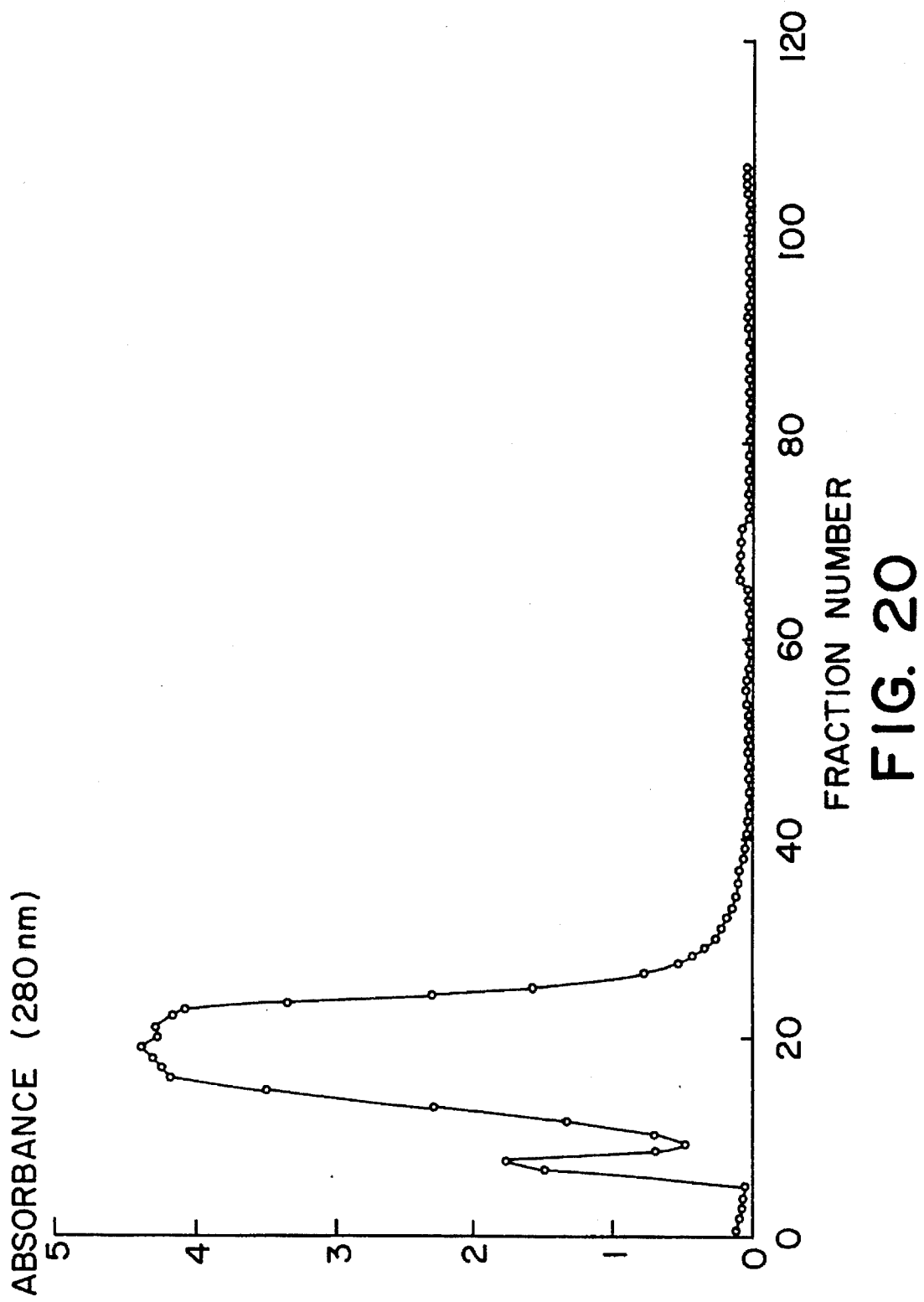
FIG. 20 shows a second elution profile using a different column.

A. second gel filtration separation was performed on a Sephadex G75 column (25.5 cm height, i.d. 1.5 cm.). This Sephadex G75 column was washed and equilibrated with phosphate buffer, 0.075M, pH 7.0 and a flow rate of 0.8 ml/min. A total of 108 fractions (2 ml per fraction) were collected in 12 hrs. A very sharp enzyme activity peak assayed by method II was observed, matching closely with optical density peak at O.D.280. (FIG. 20).

Indigo degrading activity was retained after dialysis

A lyophilized enzyme preparation (0.33 gm) was dissolved in 1 ml of 0.01M phosphate buffer, pH 7.1. This preparation was transferred into a Spectrapor membrane tubing No. 1, 23 mm width, with molecular cut-off point of 6,000–8,000D. It was dialysed against 2L of 0.01M phosphate buffer, pH 7.1 at 4° C. With constant stirring and 3 changes of buffer every 3 hrs. The indigo degrading activity was retained inside the dialysis tube. Table 6 below showed that considerable indigo degrading ability is retained in the dialysed sample in comparison with the undialysed sample.

Inactivation by autoclave and high temperature

Figure 21:
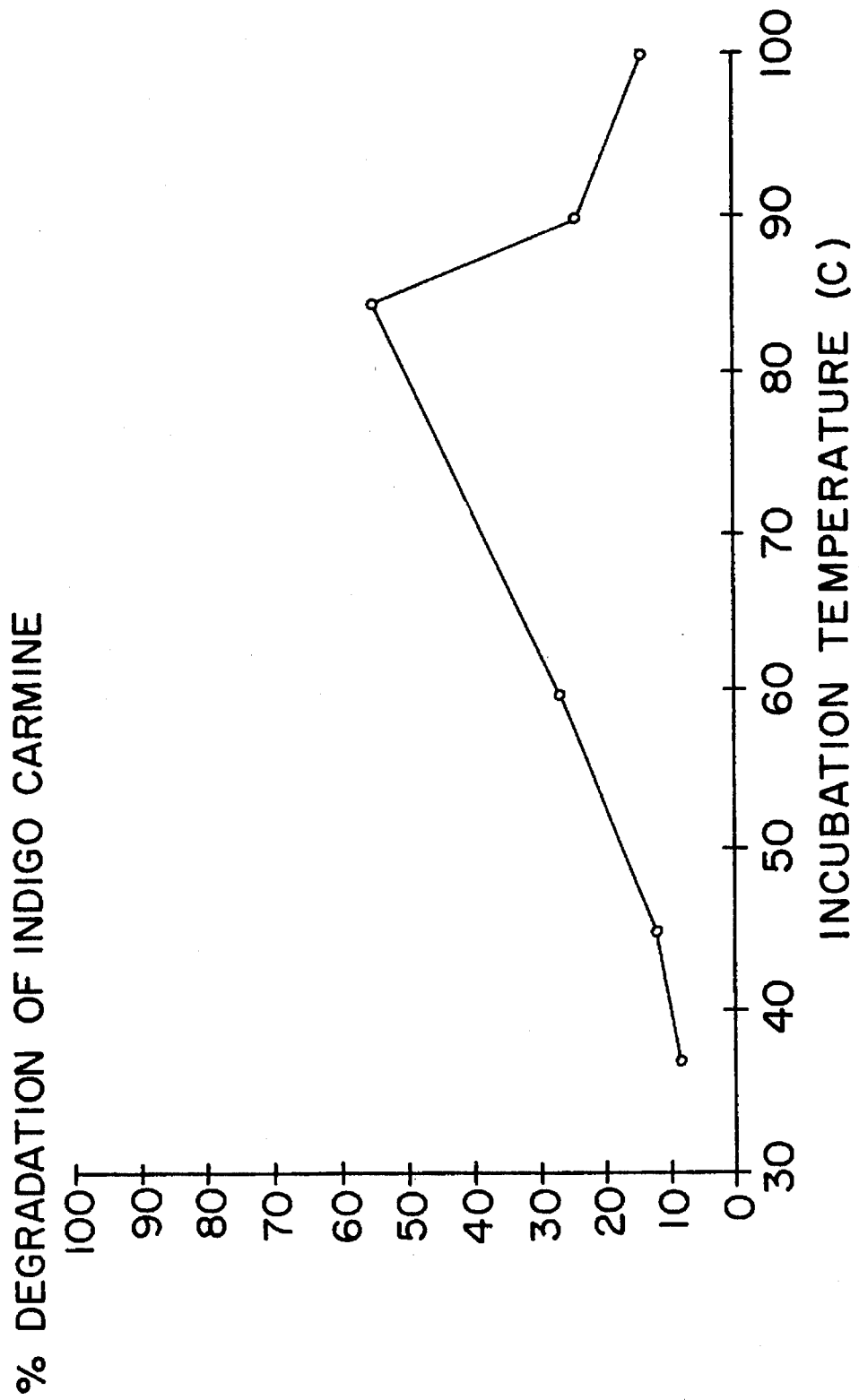
FIG. 21 shows a temperature profile of the indigo degrading enzyme extracted from H-12.
Figure 22:
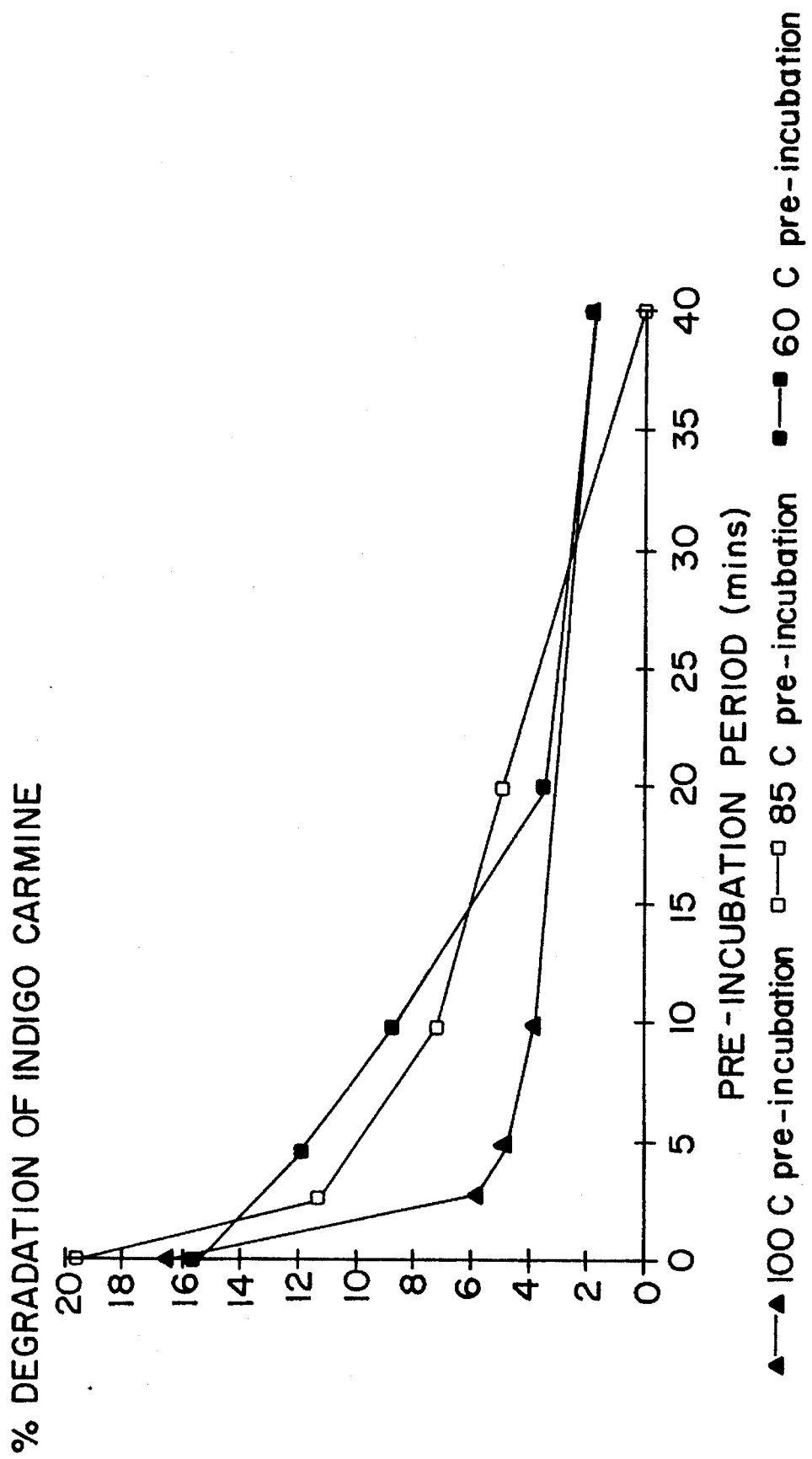
FIG. 22 shows the thermal stability of the indigo degrading enzyme extracted from H-12.

The indigo and indigo carmine degrading enzyme showed maximal activity with the substrate when incubated at 80° C. (FIG. 21). However, if the enzyme was pre-incubated at high temperature, there was a obvious loss of activity, which was proportional to the temperature and the duration of preincubation (FIG. 22).

When this crude enzyme preparation was autoclaved, all its ability to degrade indigo carmine was completely lost.

Activation or stabilization by cysteine and EDTA

The degradation ability of indigo and indigo carmine by the lyophilized enzyme preparation was significantly increased by the addition of cysteine or mercaptoethanol as well as by EDTA. The enhancement of activity by cysteine or mercaptoethanol is consistent with the presence of sulfhydryl group for the degradative activity.

B. Catalytic properties

Degradation kinetics using indigo carmine as substrate

Figure 23:
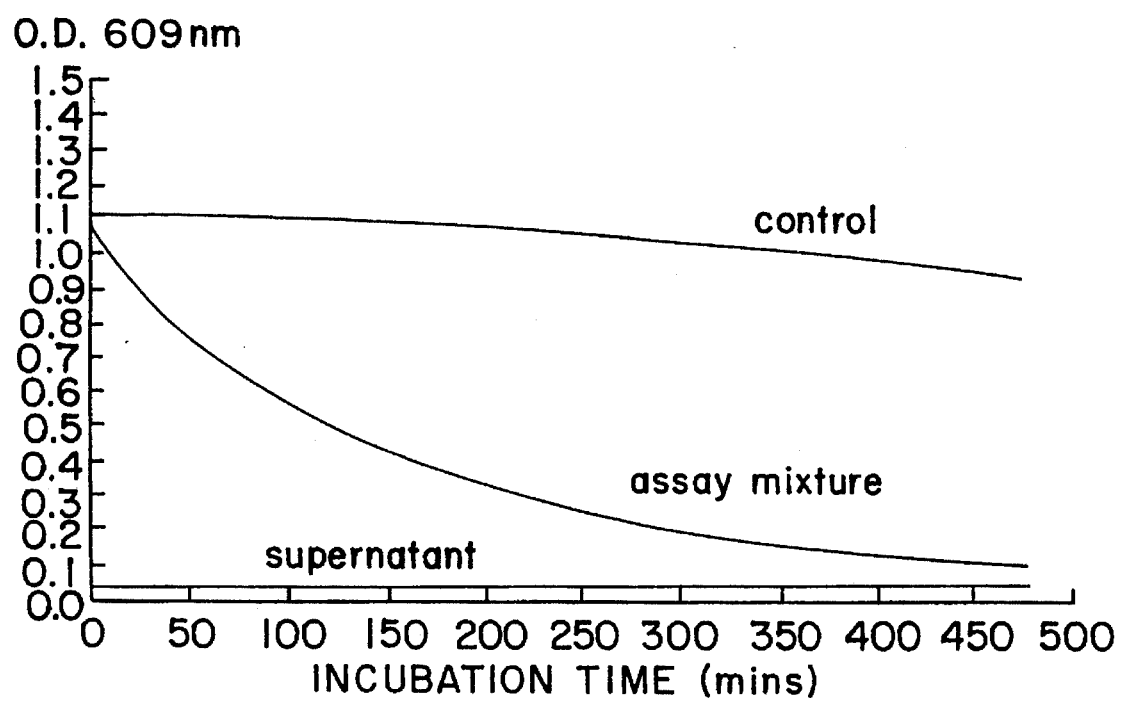
FIG. 23 shows the degradation kinetics of the enzyme extracted from H-12.
Figure 24:
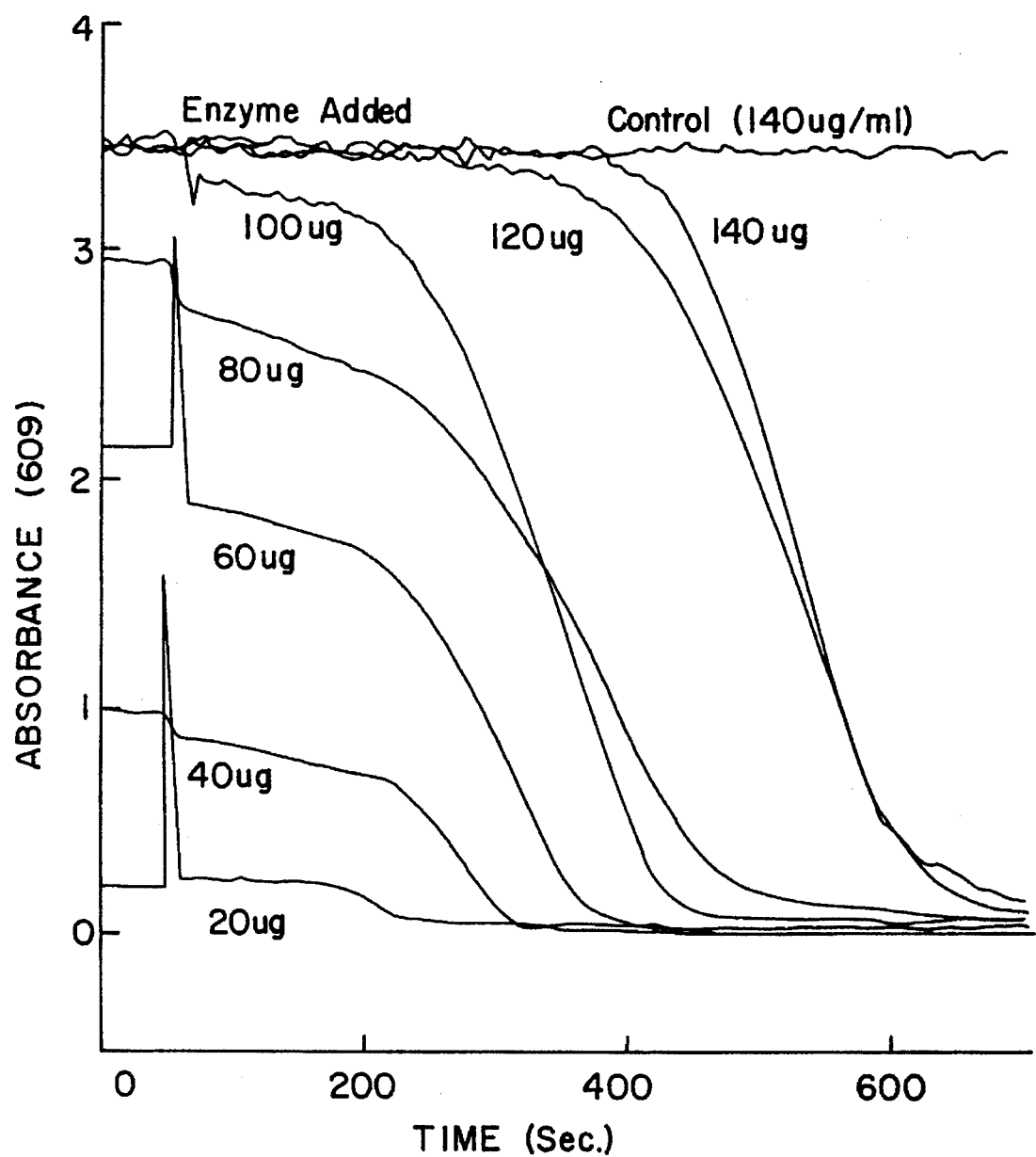
FIG. 24 shows different rates of degradation at different concentrations of the substrate, indigo carmine, with the same concentration of enzyme extracted from H-12.

The degradation kinetics of indigo carmine by the crude enzyme preparation (measured by method II) is presented in FIG. 23. The rate of degradation is proportional to the substrate concentration at a given concentration of the degradative substance, showing that the process is catalytic. See FIG. 24

Km measurements

The Km was determined using 0.2 mg/ml lyophilized enzyme preparation with variable indigo carmine concentrations. Before addition of the enzyme, the assay mixture (Method I) containing indigo carmine was bubbled with nitrogen gas to remove dissolved oxygen. After introducing into the DU-7 spectrophotometer to obtain an initial O.D. reading, the enzyme was added and mixed, then mineral oil was added to cover the surface to prevent diffusion of oxygen into the assay mixture. There was a lag period followed by a rapid and linear degradation with a rate proportional to the amount of substrate added. From Lineweaver-Burk plot of this second phase kinetics, the Km value was determined to be 0.328 mM and the Vmax 0.15 umol/sec.

Enzyme Concentration Dependence

Figure 25:
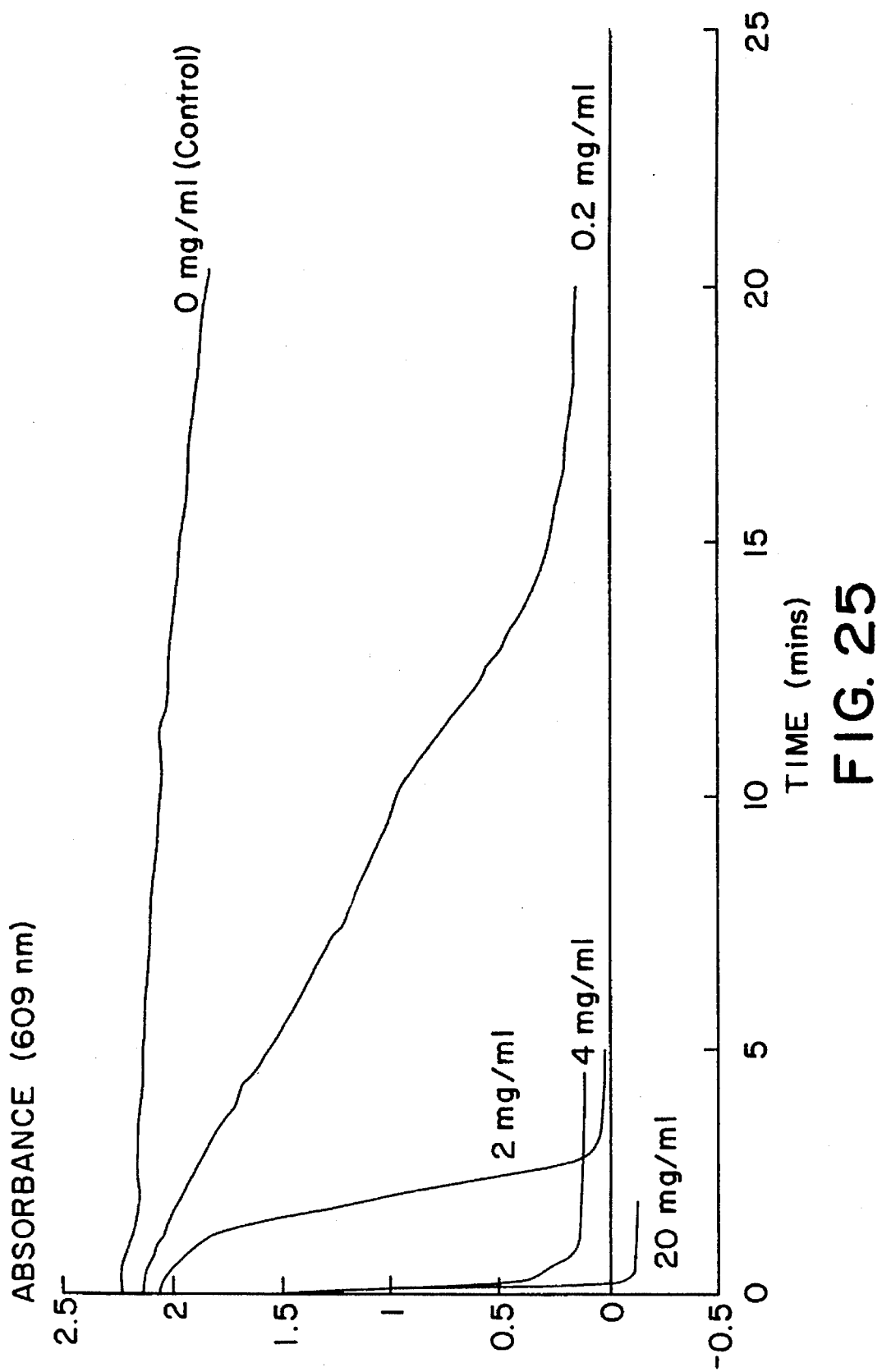
FIG. 25 shows different rates of degradation at different concentrations of the enzyme extracted from H-12.

Because of the insolubility of indigo, indigo carmine was used to measure the enzyme kinetics in a spectrophotometer at different enzyme concentrations. At 100 µg/ml indigo carmine as starting substrate concentration (method I, 45° C., pH 6.1), the rate of degradation was proportional to the amount of enzyme present (FIG. 25).

pH Optimum

Figure 26:
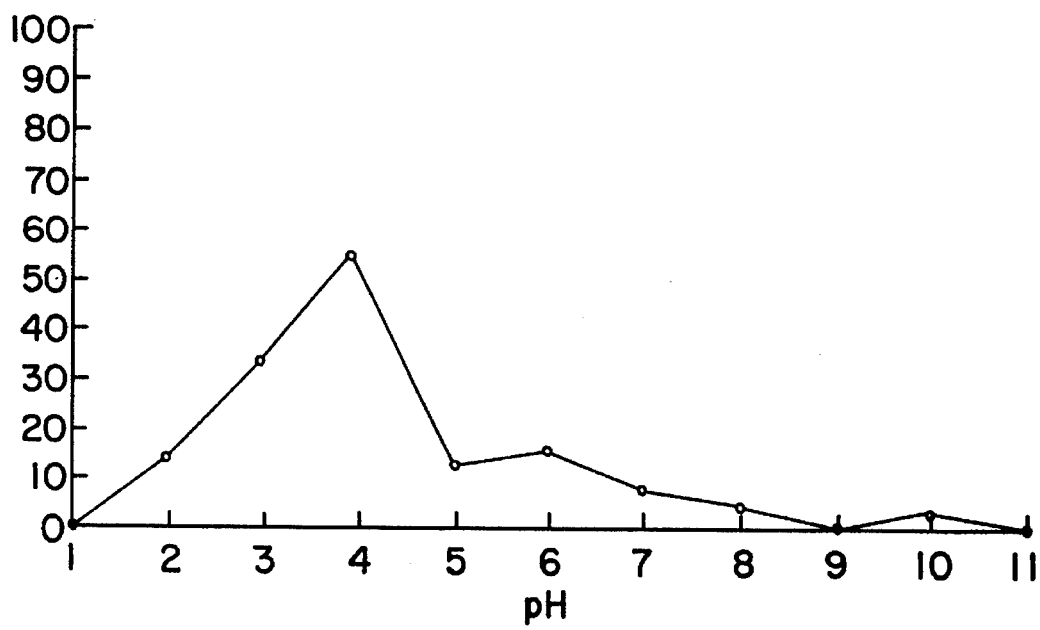
FIG. 26 shows the activity of the enzyme extracted from H-12 at different pH's.

Enzyme catalysis is usually pH dependent because of the necessary ionic state of the active site while non-enzymatic catalysis normally does not show significant pH dependency. The degradation of indigo carmine (measured by method II) showed significant pH dependence. FIG. 26 demonstrates that the optimal pH is around pH 3–4.

TABLE 5

Enzyme activity of fractions from Sephadex G50

| Samples | O.D. 609 | Indigo conc. (µg/ml) | Amount (µg) | Degraded (%) |
|---|---|---|---|---|
| Control 1 | 0.612 | 107.6 | — | — |
| Control 2 | 0.625 | 109.9 | — | — |
| Fraction 11 | 0.491 | 86.3 | 22.45 | 20.6 |
| Fraction 27 | 0.538 | 94.6 | 14.2 | 13.05 |
| Fraction 50 | 0.636 | 111.8 | 0 | 0 |
| Fraction 60 | 0.610 | 107.3 | 0 | 0 |

TABLE 6

Effect of dialysis on enzyme activity

| Samples | O.D. 609 | Indigo remain (µg) | Indigo degraded (µg) | % indigo degraded |
|---|---|---|---|---|
| Control 1 | 0.557 | 97.53 | 0 | 0% |
| Control 2 | 0.635 | 111.65 | 0 | 0% |
| | | Average 104.79 | | |
| Undialysed enzyme 1 | 0.181 | 31.82 | | |
| Undialysed enzyme 2 | 0.219 | 38.51 | 69.62 | 66.44 |
| | | Average 35.17 | | |
| Dialysed enzyme 1 | .378 | 66.46 | | |
| Dialysed enzyme 2 | 0.345 | 60.66 | 41.23 | 39.35 |
| | | Average 63.56 | | |

Removal of indigo on denim fabric surface Enzymatic removal of indigo by H-12 on denim fabric surface was demonstrated. This application encountered difficulty in the beginning probably due to the inaccessibility of the enzyme to the indigo particles trapped in the cotton fibers or because of certain surface coating that bar the proper contact.

Figure 27A:
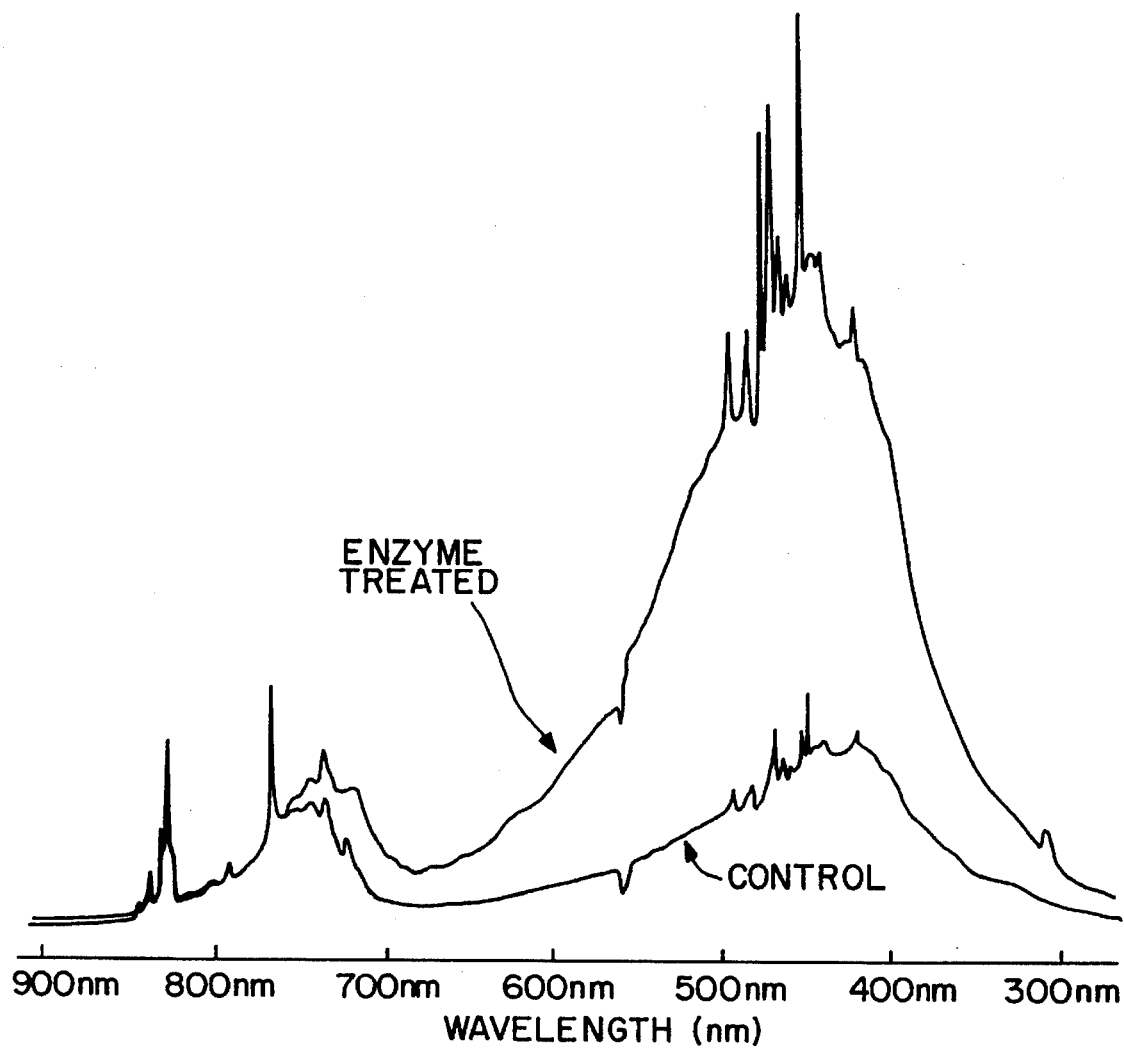
Figs. 27a–27b show spectra demonstrating the removal of indigo from denim fabric.
Figure 27B:
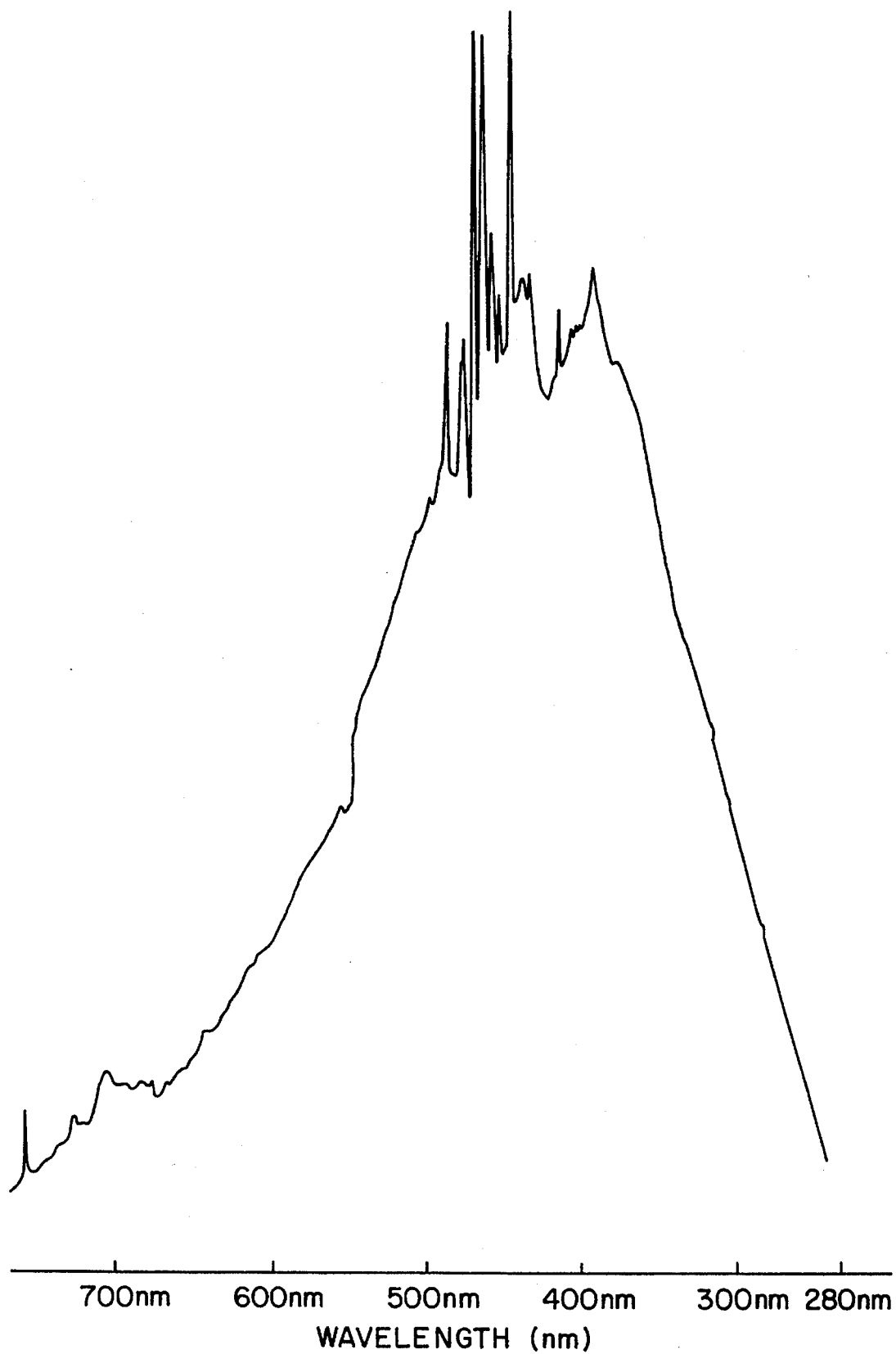

Such barriers gradually break down. The use of PVP (polyvinyl pyrrolidone), a chemical used for cell fusion, helps the enzyme to reach the trapped indigo, and leads to a significant removal of indigo from the denim fabric. The detailed conditions are given in Table 7. The results can be observed as a much paler blue color compared to the deep blue of the denim fabric, or can be measured by the reflection spectrum using a xenon light source. As shown in FIG. 28a, the intensity of the reflection spectrum by the enzyme-treated fabric is much stronger, 5.0 unit or 16%, indicating that it is a much better reflecting surface or lighter in color, while the control, the denim fabric without enzyme treatment retains the natural deep blue color, and gives a low reflection intensity 1.5 unit or 4.8%. FIG. 27a shows the background xenon lamp spectrum, 31.2 unit or 100% with ¼ ×intensity.

These are preliminary results and conditions have not been optimized, but these results point out that this indigo degrading enzyme can remove indigo in the denim fabric, and the barrier encountered previously has been broken.

TABLE 7

Conditions for removal of indigo in denim fabric

| | |
|---|---|
| 1. Enzyme concentration: | Lyophilized enzyme preparation, 0.067 mg/ml or 0.08 µg/protein ml |
| 2. PVP concentration: | 1.67% |
| 3. Buffer system: | EDTA - cysteine, pH 6.1 |
| 4. Duration of incubation: | 7 days |
| 5. Temperature: | 37° C. |
| 6. Volume of enzyme solution: | 6 ml |
| 7. Area of denim fabric: | 3 × 2 cm² |
| Experiment | Control |
| Denim fabric + PVP + buffer + enzyme | Denim fabric + PVP + buffer |
| | Results |
| Blue color changes from deep blue to pale blue Reflection spectrum is much higher indicating stronger reflection, 5.0 units or 16% as shown in FIG. 28a | No change of color, as deep blue as before treatment Reflection spectrum is relatively low, 1.5 unit or 4.8%, as shown in control in FIG. 28a. The mirror reflection is 31.2 units or 100% as shown in Fig. 28b |

In summary of these studies, a substance secreted by a microbial system was found to degrade indigo and its sulfonated derivative indigo carmine. The following is a summary of the characteristics of this system and evidence in support of the substance being a thermostable enzyme.

- The indigo-degrading activity is secreted into the medium by the microbial strain.
- The indigo-degrading ability can be inactivated by protease.
- The indigo-degrading ability lies in a fraction corresponding to molecular weight 40,000–60,000 Dalton by Sephadex G50/G75 columns chromatography.
- The indigo-degrading activity is not dialyzable by a dialysis tube of molecular weight cut off at 6,000–8,000 Daltons.
- The indigo-degrading activity is thermostable up to 80° C. but is completely inactivated by autoclaving.
- The indigo-degrading activity has a pH optimum 3 to 4.
- The indigo-degrading activity is enhanced by EDTA, cysteine, and mercaptoethanol.
- The kinetics of indigo degradation with indigo carmine as a substrate is consistent with a two-step reaction. The Km value for the second step is measured to be 0.328 mM.

It is also contemplated that the gene or the portion of the gene relevant to indigo and indigo-carmine degradation derived from any of the microorganisms mentioned above can be isolated and cloned into other organisms for such applications.

While the invention has been described by reference to specific embodiments, this was for purposes of illustration only. Numerous alternative embodiments will be apparent to those skilled in the art and are considered to be within the scope of the invention.

We claim:

1. An enzyme extracted from a strain of a bacteria deposited as ATCC 55396 or mutants thereof, said enzyme being capable of degrading indigo and indigo carmine.

2. A method for degrading indigo or indigo carmine comprising contacting the indigo or indigo carmine with an enzyme extracted from a bacteria of strain ATCC 55396 or mutants thereof.

* * * * *

UNITED STATES PATENT AND TRADEMARK OFFICE
CERTIFICATE OF CORRECTION

PATENT NO. : 5,457,043
DATED : October 10, 1995
INVENTOR(S) : Kai-Keung Mark and Walter Ho It is certified that error appears in the above-identified patent and that said Letters Patent is hereby corrected as shown below:

On the title page,
item "[73] Assignee: Hong Kong Institute of Biotechnology, Shatin, Hong Kong"

to

--[73] Assignee: Chinese University of Hong Kong, The Shatin, New Territories, Hong Kong--

Signed and Sealed this

Thirtieth Day of July, 1996

Attest:

BRUCE LEHMAN

Attesting Officer    Commissioner of Patents and Trademarks